United States Patent
Claremon et al.

[11] Patent Number: 5,633,251
[45] Date of Patent: May 27, 1997

[54] N-2,3-DIHYDRO-1-(2-PROPYL)-2-OXO-5-PHENYL-1H-1,4-BENZODIAZEPINES

[75] Inventors: David A. Claremon, Maple Glen; Nigel Liverton, Harleyville; Harold G. Selnick, Ambler, all of Pa.

[73] Assignee: Merck & Co., Inc., Rahway, N.J.

[21] Appl. No.: 516,467

[22] Filed: Aug. 17, 1995

Related U.S. Application Data

[63] Continuation-in-part of Ser. No. 292,449, Aug. 18, 1994, abandoned.

[51] Int. Cl.⁶ .................. C07D 243/24; A61K 31/395
[52] U.S. Cl. ............................................. 514/221; 540/509
[58] Field of Search .................... 514/221; 540/509

[56] References Cited

U.S. PATENT DOCUMENTS

| | | | |
|---|---|---|---|
| 4,820,834 | 4/1989 | Evans et al. | 540/504 |
| 5,153,191 | 10/1992 | Woodruff | 514/221 |
| 5,166,151 | 11/1992 | Freidinger et al. | 514/215 |
| 5,220,018 | 6/1993 | Bock et al. | 540/509 |
| 5,324,726 | 6/1994 | Bock et al. | 514/221 |

FOREIGN PATENT DOCUMENTS

| | | |
|---|---|---|
| 0514133A1 | 11/1992 | European Pat. Off. . |
| 0538945A1 | 4/1993 | European Pat. Off. . |
| WO93/02078 | 2/1993 | WIPO . |
| WO93/08176 | 4/1993 | WIPO . |
| WO93/07131 | 4/1993 | WIPO . |
| WO93/19063 | 9/1993 | WIPO . |
| WO93/17011 | 9/1993 | WIPO . |

*Primary Examiner*—John M. Ford
*Attorney, Agent, or Firm*—Francis P. Bigley; Mark R. Daniel

[57] ABSTRACT

This invention is concerned with novel compounds represented by structural formula I

FORMULA I

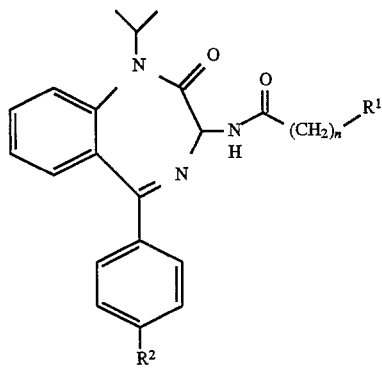

where $R^1$ is

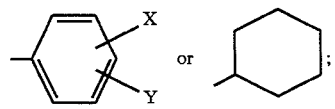

X and Y are independently hydrogen, fluoro, chloro, bromo, iodo, or trifluoromethyl;

n is 0, 1 or 2; and $R^2$ is hydrogen, fluoro, chloro, bromo, iodo, or trifluoromethyl, methyl, or methoxy;
as the racemates, mixtures of enantiomers, individual diastereomers or individual enantiomers, and pharmaceutically acceptable crystal forms, salts, or hydrates thereof.

11 Claims, No Drawings

N-2,3-DIHYDRO-1-(2-PROPYL)-2-OXO-5-PHENYL-1H-1,4-BENZODIAZEPINES

CROSS REFERENCE

This is a continuation in part of U.S. patent application Ser. No. 08/292,449 which was filed on Aug. 18, 1994, now abandoned.

BACKGROUND OF THE INVENTION

Arrhythmias often occur as complications to cardiac diseases such as myocardial infarction and heart failure. In a serious case, arrhythmias give rise to ventricular fibrillation and can cause sudden death.

Though various antiarrythmic agents are now available on the market, agents which exhibit both satisfactory effects and high safety profiles have not been obtained. For example, antiarrythmic agents of Class I, according to the classification of Vaughan-Williams, which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

SUMMARY OF THE INVENTION

This invention is concerned with novel compounds represented by structural formula I

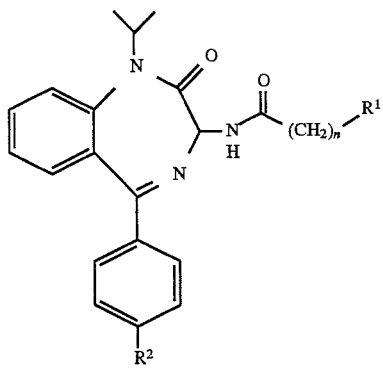

where
R¹ is

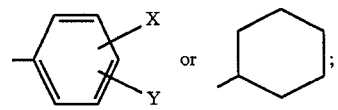

X and Y are independently hydrogen, fluoro, chloro, bromo, iodo, or trifluoromethyl;

n is 0, 1 or 2; and $R^2$ is hydrogen, fluoro, chloro, bromo, iodo, or trifluoromethyl, methyl, or methoxy;

as the racemates, mixtures of enantiomers, individual diastereomers or individual enantiomers, and pharmaceutically acceptable crystal forms, salts, or hydrates thereof, which are useful as antiarrhythmic agents.

The compounds of the present invention may have asymmetric centers and occur as racemates, mixtures of enantiomers, individual diastereomers, or as individual enantiomers with all isomeric forms being included in the present invention. The invention is also concerned with pharmaceutical formulations comprising one of the novel compounds as an active ingredient.

The invention is also concerned with a method of treating arrhythmia by the administration of one of the novel compounds or formulation thereof to a patient in need of such treatment.

DETAILED DESCRIPTION OF THE INVENTION

The novel compounds of this invention have structural formula I

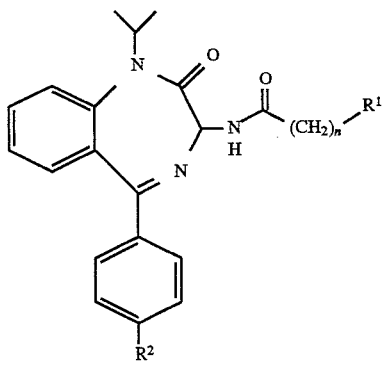

where
$R^1$ is

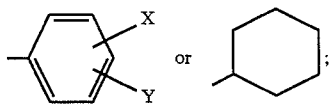

X and Y are independently hydrogen, fluoro, chloro, bromo, iodo, or trifluoromethyl;

n is 0, 1 or 2; and $R^2$ is hydrogen, fluoro, chloro, bromo, iodo, or trifluoromethyl, methyl, or methoxy;

as the racemates, mixtures of enantiomers, individual diastereomers or individual enantiomers, and pharmaceutically acceptable crystal forms, salts, or hydrates thereof. These compounds include pharmaceutically acceptable crystal forms and hydrates of the compounds of Formula I, which are antiarrhythmic agents.

The compounds of the present invention may have asymmetric centers and occur as racemates, mixtures of enantiomers, individual diastereomers, or as individual enantiomers with all isomeric forms being included in the present invention.

One preferred embodiment of the present invention is (+)-2-[2,4-Bis(trifluoromethyl)phenyl]-N-[3R-2,3-dihydro-1-(2-propyl)-2-oxo-5-phenyl-1H-benzo[e][1,4]diazepin-3-yl]acetamide

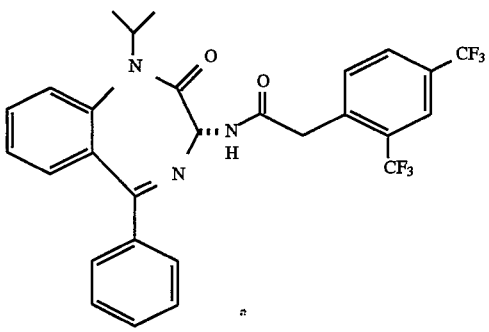

Another embodiment of the novel compounds of this invention is (+)-3,5-Dichloro-N-[3R-2,3-dihydro-1-(2-propyl)-2-oxo-5-phenyl-1H-benzo[e][1,4]diazepin-3-yl] benzamide.

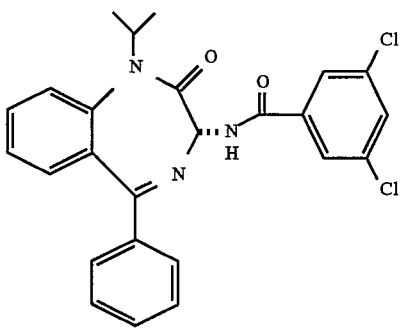

A second embodiment of the novel compounds of this invention is (+)-3-Cyclohexyl-N-[2,3-dihydro-1-(2-propyl)-2-oxo-5-phenyl-1H-benzo[e][1,4]diazepin-3-yl] propanamide

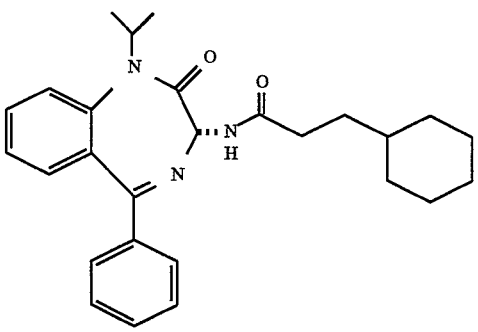

Still another embodiment of the novel compounds of this invention is (+)-2-(3,4-Dichlorophenyl)-N-[2,3-dihydro-1-(2-propyl)-2-oxo-5-phenyl-1H-benzo[e][1,4]diazepin-3-yl] acetamide

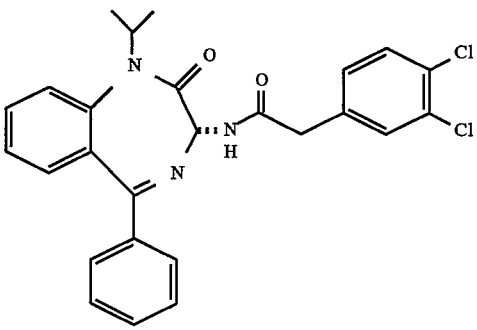

Other examples of the compounds of this invention include:

(+)-2-(3,5-Dichlorophenyl)-N-[2,3-dihydro-1-(2-propyl)-2-oxo-5-phenyl-1H-benzo[e][1,4]diazepin-3-yl]acetamide

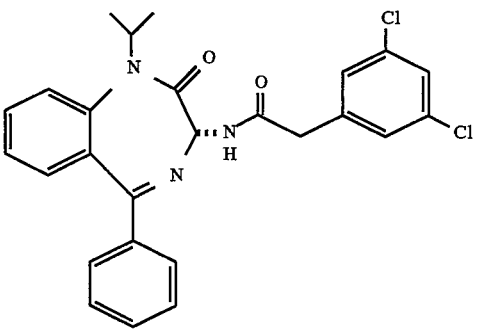

(+)-3-(2,4-Dichlorophenyl)-N-[2,3-dihydro-1-(2-propyl)-2-oxo-5-phenyl-1H-benzo[e][1,4]diazepin-3-yl]propanamide

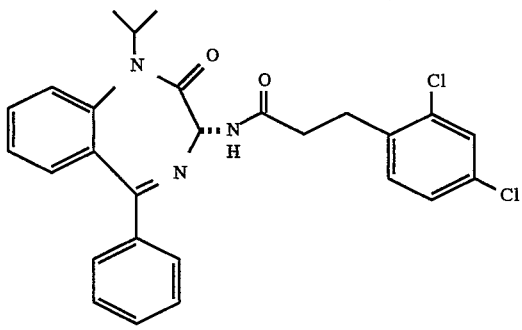

(−)-3-(2,4-Dichlorophenyl)-N-[3S-2,3-dihydro-1-(2-propyl)-2-oxo-5-phenyl-1H-benzo[e][1,4]diazepin-3-yl]propanamide

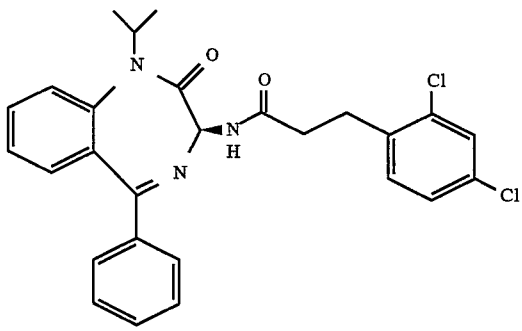

(−)-3-(3,4-Dichloro)-N-[3S-2,3-dihydro-1-(2-propyl)-2-oxo-5-
phenyl-1H-benzo[e][1,4]diazepin-3-yl]benzamide

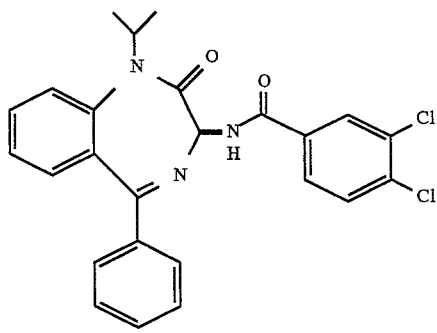

(+)-2-Adamantan-1-yl-N-[3R-2,3-dihydro-1-(2-propyl)-2-oxo-5-
phenyl-1H-benzo[e][1,4]diazepin-3-yl]acetamide

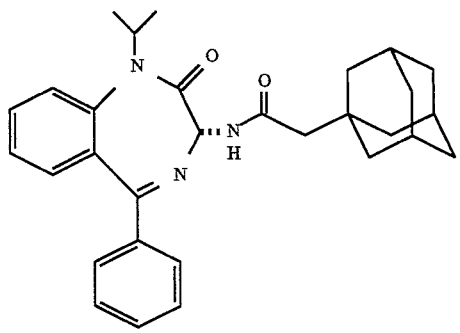

(+)-4-Cyclohexyl-N-[3R-2,3-dihydro-1-(2-propyl)-2-oxo-5-phenyl-
1H-benzo[e][1,4]diazepin-3-yl]butanamide

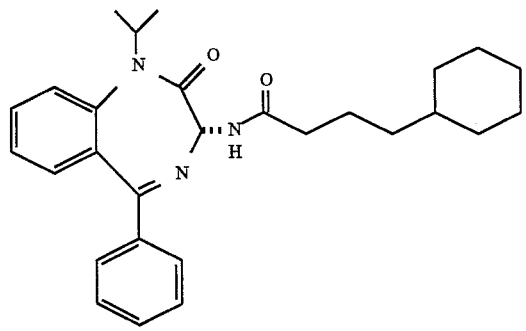

(+)-Adamantan-1-yl-N-[3R-2,3-dihydro-1-(2-propyl)-2-oxo-5-
phenyl-1H-benzo[e][1,4]diazepin-3-yl]carboxamide

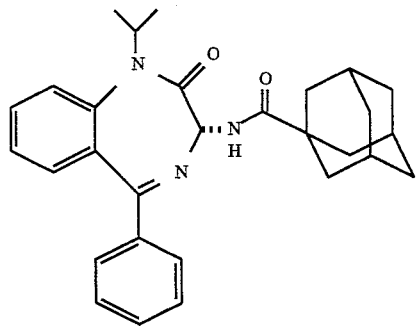

(+)-2-[3,5-Bis(trifluoromethyl)phenyl]-N-[3R-2,3-dihydro-1-
(2-propyl)-2-oxo-5-phenyl-1H-benzo[e][1,4]diazepin-3-yl]acetamide

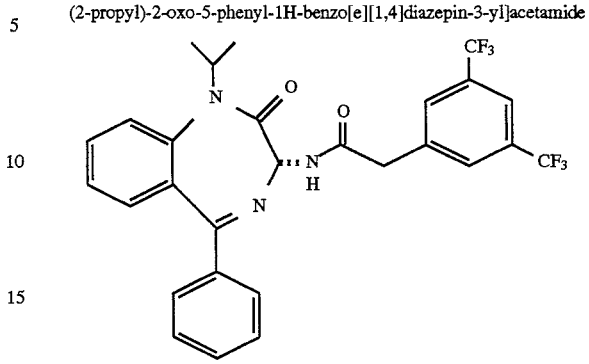

(+)-2-(2,4-Dichlorophenyl)-N-[3R-2,3-dihydro-1-(2-propyl)-2-oxo-
5-phenyl-1H-benzo[e][1,4]diazepin-3-yl]acetamide

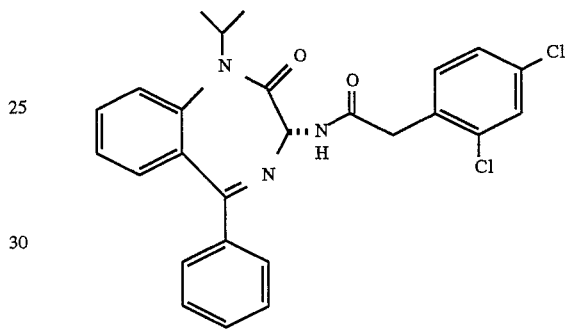

(+)-3-Chloro-N-[3R-2,3-dihydro-1-(2-propyl)-2-oxo-5-phenyl-1H-
1,4-benzodiazepin-3-yl]benzamide

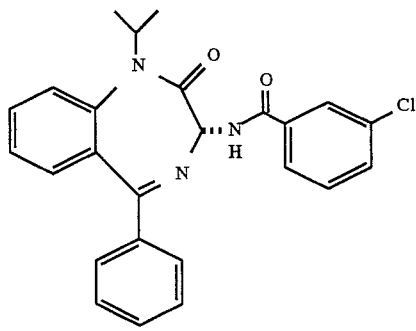

(+)-4-Chloro-N-[3R-2,3-dihydro-1-(2-propyl)-2-oxo-5-phenyl-1H-
1,4-benzodiazepin-3-yl]benzamide

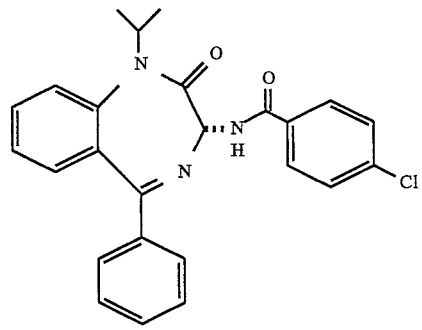

(+)-2-(3-Chlorophenyl)-N-[3R-2,3-dihydro-1-(2-propyl)-2-oxo-5-phenyl-1H-benzo[e][1,4]diazepin-3-yl]acetamide

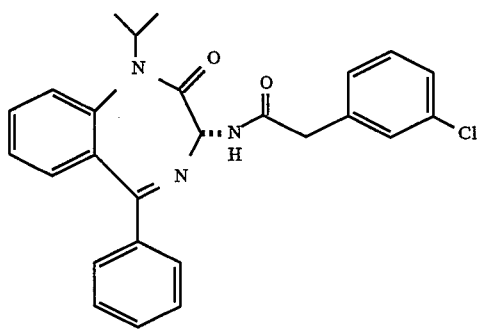

(+)-3-Bromo-4-chloro-N-[3R-2,3-dihydro-1-(2-propyl)-2-oxo-5-phenyl-1H-benzo[e][1,4]diazepin-3-yl]benzamide

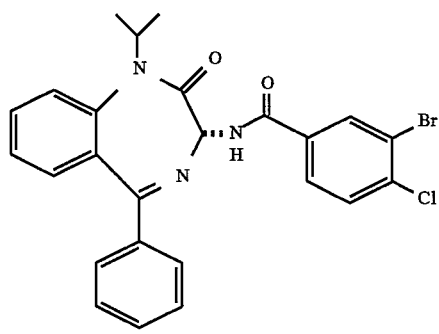

3,4-Dichloro-N-[2,3-dihydro-1-(2-propyl)-2-oxo-5-(2-fluorophenyl)-1H-benzo[e][1,4]diazepin-3-yl]benzamide

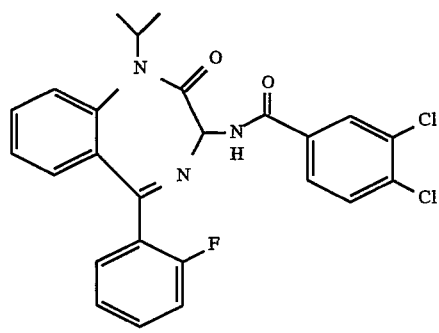

(+)-3-Bromo-N-[3R-2,3-dihydro-1-(2-propyl)-2-oxo-5-phenyl-1H-benzo[e][1,4]diazepin-3-yl]benzamide

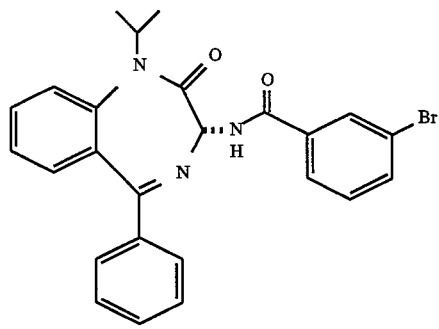

3-Cyclohexyl-N-[2,3-dihydro-1-(2-propyl)-2-oxo-5-(2-fluorophenyl)-1H-benzo[e][1,4]diazepin-3-yl]propanamide

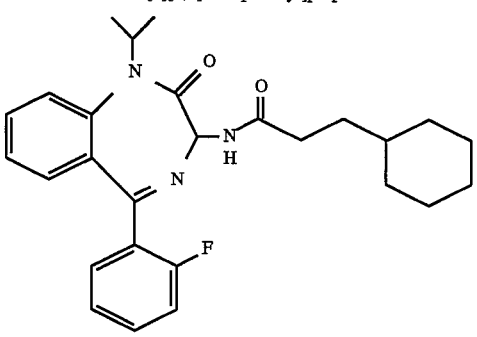

(−)-3-(3,5-Dichloro)-N-[3S-2,3-dihydro-1-(2-propyl)-2-oxo-5-phenyl-1H-benzo[e][1,4]diazepin-3-yl]benzamide

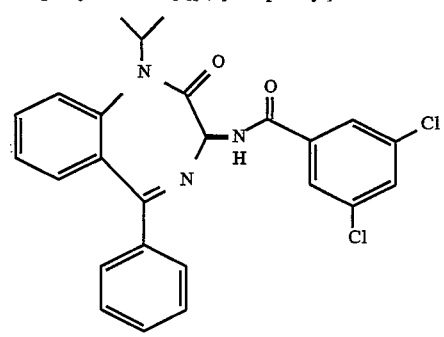

(+)-N-[3R-2,3-dihydro-1-(2-propyl)-2-oxo-5-phenyl-1H-1,4-benzodiazepin-3-yl]benzamide

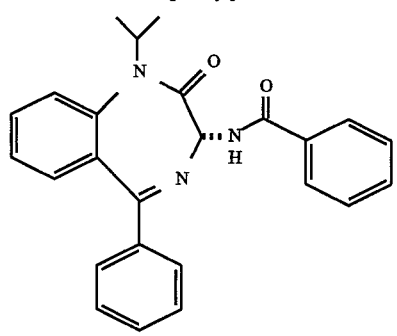

(+)-2-(3-Trifluoromethylphenyl)-N-[3R-2,3-dihydro-1-(2-propyl)-2-oxo-5-phenyl-1H-benzo[e][1,4]diazepin-3-yl]acetamide

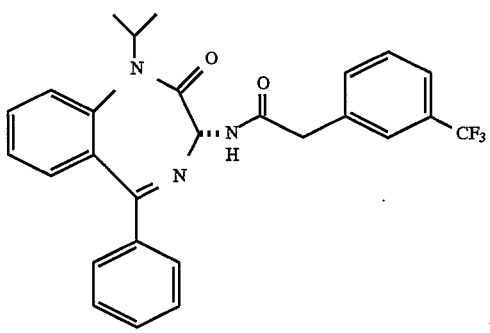

(+)-3,5-Bis(trifluoromethyl)-N-[3R-2,3-dihydro-1-(2-propyl)-2-oxo-5-phenyl-1H-benzo[e][1,4]diazepin-3-yl]benzamide

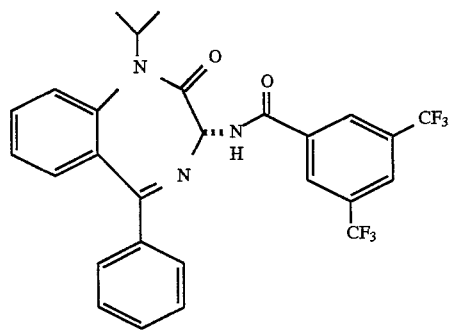

(+)-2-(2-Trifluoromethylphenyl)-N-[3R-2,3-dihydro-1-(2-propyl)-2-oxo-5-phenyl-1H-benzo[e][1,4]diazepin-3-yl]acetamide

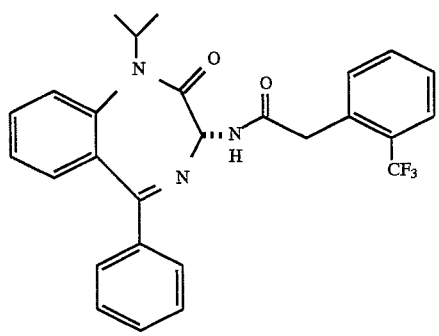

(+)-2-(4-Trifluoromethylphenyl)-N-[3R-2,3-dihydro-1-(2-propyl)-2-oxo-5-phenyl-1H-benzo[e][1,4]diazepin-3-yl]acetamide

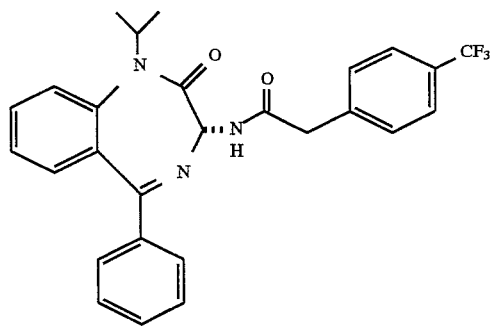

(+)-2-Phenyl-N-[3R-2,3-dihydro-1-(2-propyl)-2-oxo-5-phenyl-1H-benzo[E][1,4]diazepin-3-yl]acetamide

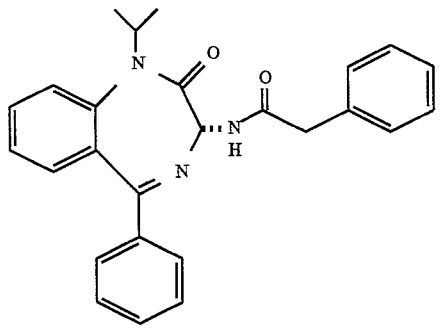

(−)-2-(3,5-Dichlorophenyl)-N-[3S-2,3-dihydro-1-(2-propyl)-2-oxo-5-phenyl-1H-benzo[e][1,4]diazepin-3-yl]acetamide

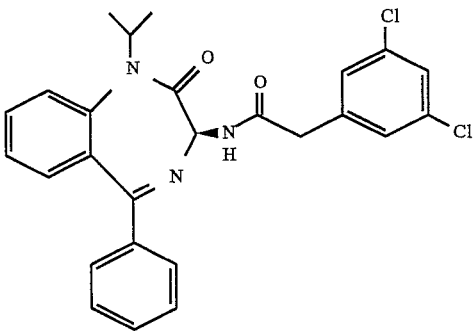

(−)-2-Hydroxy-2-(4-trifluoromethylphenyl)-N-[3R-2,3-dihydro-1-(2-propyl)-2-oxo-5-phenyl-1H-benzo[e][1,4]diazepin-3-yl]acetamide

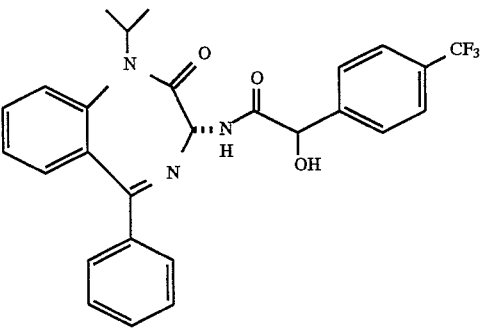

(+)-2-Hydroxy-2-(4-trifluoromethylphenyl)-N-[3R-1-(2-propyl)-2-oxo-5-phenyl-2,3-dihydro-1H-benzo[e][1,4]diazepin-3-yl]acetamide

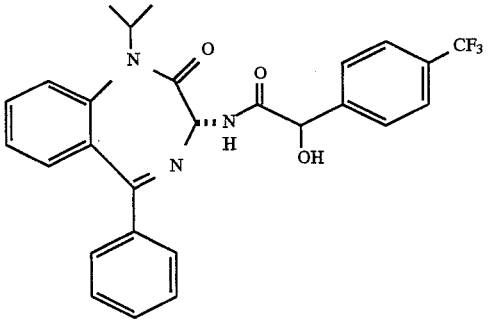

(+)-3-Cyclohexyl-N-[2,3-dihydro-1-(2-propyl)-2-oxo-5-(4-fluorophenyl)-1H-benzo[e][1,4]diazepin-3-yl]propanamide

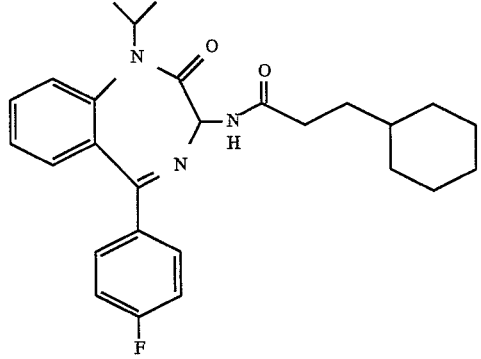

11
(+)-3,5-Dichloro-N-[2,3-dihydro-1-(2-propyl)-2-oxo-5-(4-fluorophenyl)-1H-benzo[e][1,4]diazepin-3-yl]benzamide
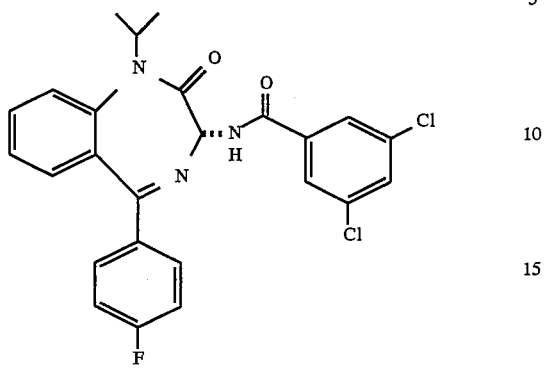
12
A novel process for preparing the compounds of this invention is schematically exemplified below in scheme, and these steps are well known in the art and/or described in the Examples that follow.
Scheme 1
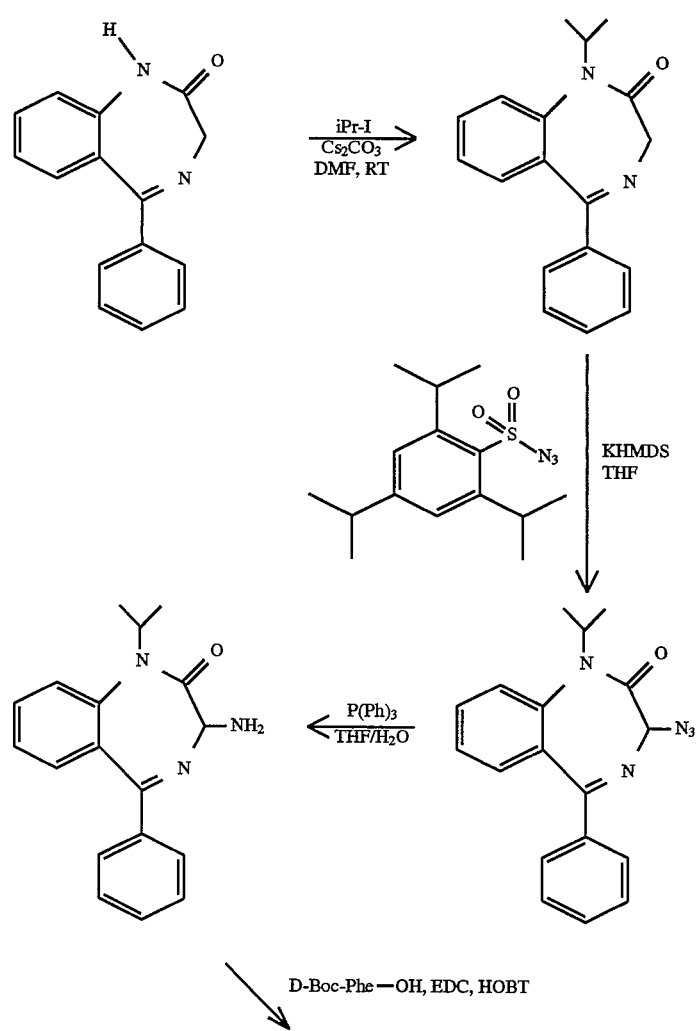

-continued
Scheme 1
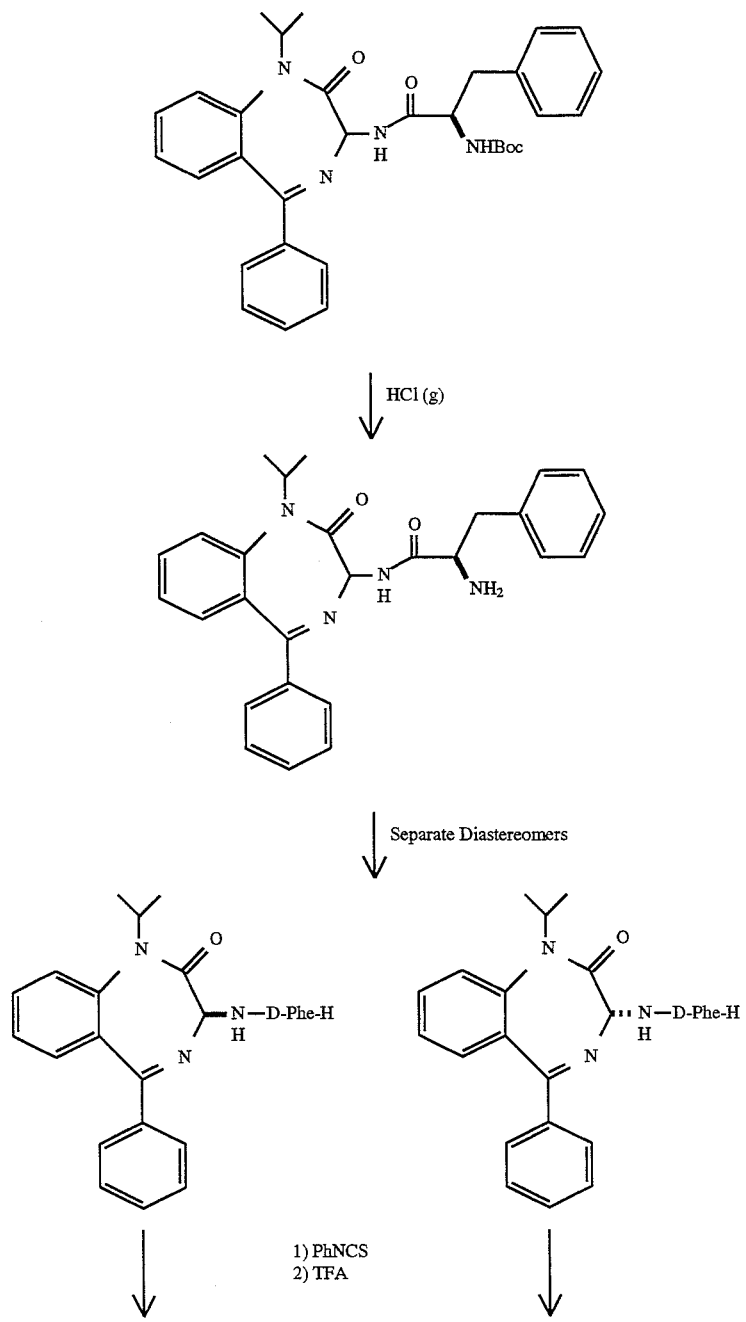
1) PhNCS
2) TFA

-continued
Scheme 1

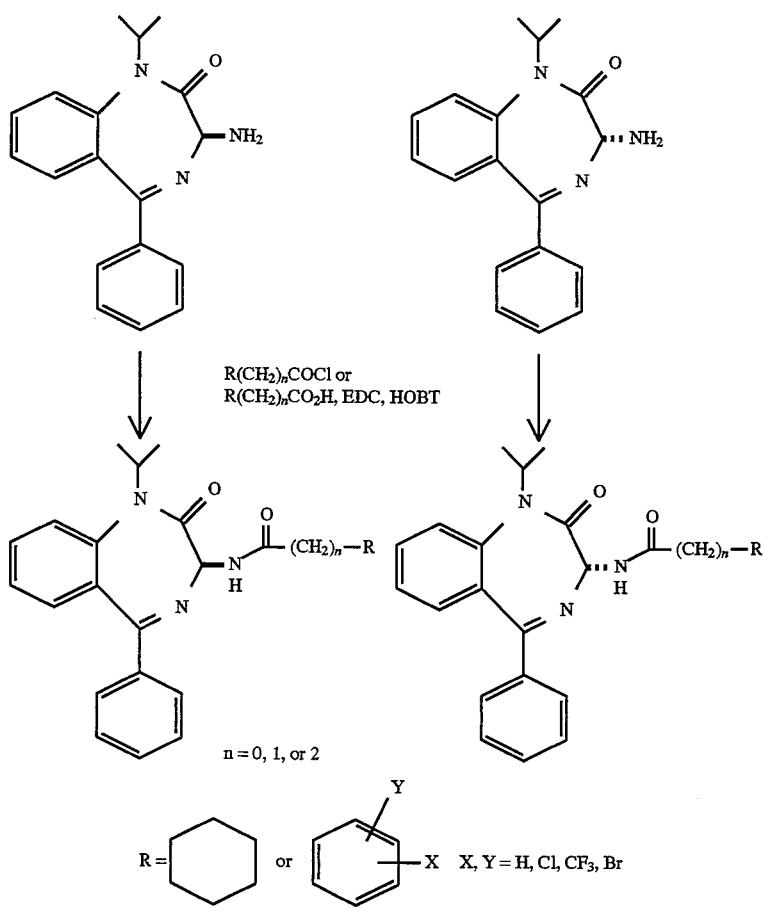

n = 0, 1, or 2

X, Y = H, Cl, CF₃, Br

The novel compounds of the present invention have the pharmacological properties required for antiarrhythmic agents of Class III, namely they demonstrate prolongation of QTc-interval, and dose dependent increases in ventricular refractoriness. This is accomplished without effecting heart rate, mean arterial pressure and PR and QRS intervals. Modest increases in LV+dP/dt (left ventricular change in pressure with time) is observed. Further, these compounds suppress the induction of PVS (Programmed Ventricular Stimulation) induced ventricular tachyarrhythmias.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 10 mg per kg of body weight per day, preferably from about 0.0001 to about 2 mg per kg of body weight per day, and more preferably by intravenous delivery of from about 0.0003 to about 0.3 mg per kg of body weight per day, or when given orally from about 0.03 to about 1 mg per kg of body weight per day, in a single dose or in 2 to 4 divided doses.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, emulsions, syrups, wafers, chewing gum, or the like prepared by art recognized procedures. The amount of active compound in such therapeutically useful compositions or preparations is such that a suitable dosage will be obtained.

These compounds can be administered as the sole active ingredient or in combination with other antiarrhythmic agents or other cardiovascular agents, such as Class I, Class II or Class IV antiarrhythmic agents, vasodilators, angiotensin converting enzyme inhibitors, angiotensin II antagonists, diuretics or digitalis.

These compounds can be administered as a method of treating arrhythmia and impaired cardiac pump functions in conjunction with defibrillators, including implantable defibrillators. These compounds reduce the frequency of defibrillator firing.

By Class I antiarrhythmic agents is meant those agents which provide for sodium channel blockade, including those compounds which exert a membrane stabilizing effect. Exemplary of this class of compounds are quinidine, procainamide, disopyramide, lidocane, tocainide, flecainide and propafenone. By Class II antiarrhythmic compounds is meant those agents which block sympathetic activity. Exemplary of this class of compounds are propranolol and acebutolol. By Class III antiarrhythmic agents is meant those compounds which prolong the effective refractory period without altering the resting membrane potential or rate of depolarization. In addition to the novel compounds of this invention, compounds such as amiodarone, bretylium and sotalol are considered to be in this class. Class IV antiarrhythmic agents are effective in calcium channel blockade. Exemplary of this class of compounds are diltiazem and verapamil. Further definition of these classes can be found in Pharma Projects, section C1B, May 1993, which is hereby incorporated by reference.

Exemplary of vasodilators are compounds such as papaverine and isosorbide dinitrat. Examples of angiotensin converting enzyme inhibitors include enalapril, lisinopril and captopril. Examples of diuretics include hydrochlorothiazide and acetazolamide. The pharmaceutical agents listed herein are examples and do not represent a complete listing of the many compounds in these classes which are contemplated by this invention.

The activity of the compounds described herein as anti-arrhythmic agents is measured by their ability to block the $I_{Ks}$ and $I_{Kr}$ currents as determined by the following test protocol.

Outward potassium currents are measured in single guinea pig ventricular myocytes using a whole-cell voltage clamp technique described in detail elsewhere (Sanguinetti and Jurkiewicz, 1990, Two components of cardiac delayed rectifier K$^+$ current: differential sensitivity to block by Class III antiarrhythmic agents. J. Gen Physiol. 96: 195–215). Myocytes are isolated by enzymatic (collagenase and protease) digestion of Langandorf perfused hearts. Single cells are then voltage clamped using 1 mm square-bore pipettes filled with 0.5M gluconate, 25 mM KCl, 5 mM K(2)ATP. Cells are bathed in a solution containing, in mM: 132 NaCl, 4 KCl, 1.2 MgCl$_2$, 10 HEPES, 10 glucose: pH 7.2, temp. 35° C.

Each cell is maintained at a holding potential of –50 mV. Test depolarizations are applied as voltage ramps from –85 to –50 mV, and as steps to –10 mV (0.5 s) and +50 mV (1.0 s). $I_{KI}$ is measured as peak outward current during the voltage ramp. $I_{Kr}$ is measured as tail currents upon repolarization from –10 mV to –50 mV. $I_{Ks}$ is measured as time-dependent current during the pulse to +50 mV. Currents are measured during control, then after exposure to drug at two different concentrations.

Employing this test the compounds described herein have an IC$_{50}$ of less than 100 nM as $I_{Ks}$ blockers. The compounds of this invention are at least 10 times more potent in the blockade of $I_{Ks}$ than the blockade of $I_{Kr}$.

EXAMPLE 1

(+)-3,5-Dichloro-N-[3R-2,3-dihydro-1-(2-propyl)-2-oxo-5-phenyl-1H-benzo[e][1,4]diazepin-3-yl]benzamide.

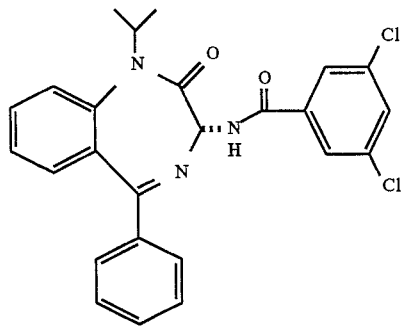

Step A: Preparation of 2,3-dihydro-1-(2-propyl)-2-oxo-5-phenyl-1H-benzo[e][1,4]diazepine A solution of 5-phenyl-1,4-benzodiazepine-2-one (*J. Org. Chem.*, 1962, 27, 3788)(50 g, 0.211 mole) in DMF (100 mL) was treated with Cesium carbonate (82.8 g, 0.254 mole) and 2-iodopropane (43.2 g, 0.254 mole). The mixture was stirred at room temperature for five hours. The reaction mixture was then poured into water (2 L) and extracted with ethyl acetate (3×1 L). The combined ethyl acetate fractions were dried over anhydrous magnesium sulfate, filtered and concentrated at reduced pressure. The residue was crystallized from ethyl ether to give 45 g (77 of the product. MP=153°–155° C.

$^1$H NMR (CDCl$_3$) δ 7.65–7.6(m, 2H), 7.60–7.35 (m, 5H), 7.35–7.20 (m, 2H), 4.72(d, J=10 Hz, 1H), 4.58 (hep, J=6.8 Hz, 1H), 3.75 (d, J=10 Hz, 1H), 1.5 (d, J=6.8 Hz, 3H), 1.2 (d, J=6.8 Hz, 3H).

Step B: Preparation of 3-Azido-2,3-dihydro-1-(2-propyl)-2-oxo-5-phenyl-1H-benzo[e][1,4]diazepine To a solution of 2,3-dihydro-1-(2,propyl)-2-oxo-5-phenyl-1H-1,4-benzodiazepine (50 g, 0.179 mole) in THF (1200 mL) at –70° C. was added a solution of potassium bis(trimethylsilyl) amide in toluene (400 mL of a 0.5N solution, 0.20 mole). The deep orange solution was then treated with a solution of triisopropylbenzenesulfonyl azide (61.1 g, 0.197 mole) in THF (200 mL). The reaction was stirred at –70° C. for 10 minutes and then treated with acetic acid (4 mL in 20 mL of THF) and warmed to room temperature over one hour. The reaction mixture was then poured into water (1.5 L) and extracted with ethyl acetate (3×500 mL). The combined ethyl acetate fractions were washed with a solution of sodium bicarbonate (300 mL), then water (2×500 mL), and then brine (500 mL). The ethyl acetate solution was then dried over anhydrous magnesium sulfate, filtered and concentrated at reduced pressure. The residue was crystallized from ethyl ether to give 48 g (84%) of the product. MP=178°–179° C.;

$^1$H NMR (CDCl$_3$) δ 7.75–7.65(m, 2H), 7.60–7.20 (m, 7H), 4.58 (hep, J=6.8 Hz, 1H),4.45(s, 1H), 1.51 (d, J=6.8 Hz, 3H), 1.26 (d, J=6.8 Hz, 3H).

Step C: Preparation of racemic 3-Amino-2,3-dihydro-1-(2-propyl)-2-oxo-5-phenyl-1H-benzo[e][1,4]diazepine To a solution of 3-azido-2,3-dihydro-1-(2,propyl)-2-oxo-5-phenyl-1H-1,4-benzodiazepine (48 g, 0.15 mole) in THF (500 mL) at room temperature was added water (40 mL) and triphenyl phosphine (90 g, 0.343 mole). The reaction was stirred at room temperature for 24 hours and concentrated at reduced pressure. The residue was partitioned between 1N HCl (1.5 L) and ether (500 mL). The ether layer was discarded and the aqueous phase was extracted with ethyl acetate (1×100 mL) which was also discarded. The aqueous phase was basified to pH 8 by careful addition of 6N sodium hydroxide solution and extracted with ethyl acetate (3×500 mL). The combined ethyl acetate phases were dried over anhydrous magnesium sulfate, filtered, and concentrated at reduced pressure. The residue was crystallized from ethyl ether to give 41.7 g (94%) of the product. MP=130°–135° C.;

$^1$H NMR (CDCl$_3$) δ 7.75–7.65 (m, 2H), 7.60–7.20 (m, 7H), 4.65 (hep, J=6.8 Hz, 1H),4.43 (s, 1H), 2.5 (br s, 2H,-NH$_2$), 1.51 (d, J=6.8 Hz, 3H), 1.26 (d, J=6.8 Hz, 3H).

Step D: Preparation of (2R)-2-Amino-3-phenyl-N-[2,3-dihydro-1-(2-propyl)-2-oxo-5-phenyl-1H-benzo[e][1,4]diazepin-3-yl]propionamide To a stirring solution of (+)-3-amino-2,3-dihydro-1-(2-propyl)-2-oxo-5-phenyl-1H-1,4-benzodiazepine (40.8 g, 139 mmol) in dimethylformamide (140 mL) was added EDC (32.0 g, 167 mmol), HOBT (22.6 g, 167 mmol) and N-BOC-D-phenylalanine (44.3 g, 167 mmol). This was stirred at ambient temperature for 2 h. The reaction was diluted with saturated aqueous sodium hydrogen carbonate (1.5 L) and extracted with ethyl acetate (3×1 L). The organic layers were combined, dried with brine, anhydrous magnesium sulfate, filtered, and evaporated under reduced pressure to give a yellow oil which was dissolved in ethyl acetate (700 mL), cooled in an ice/water bath. Hydrogen chloride gas was bubbled into the solution for 3 h. The reaction mixture was concentrated under reduced pressure and the resulting foam was dissolved in ethyl acetate (1 L) and saturated aqueous sodium hydrogen carbonate (1 L). The layers were separated and the aqueous layer was extracted with ethyl acetate again (2×1 L). The organic layers were combined, dried with brine, anhydrous magnesium sulfate, filtered, and evaporated under reduced pressure to give a white solid, which was chromatographed over silica (2.5 kg) with ethyl acetate. The faster running diastereomer was recovered as a white solid (22.0 g, 72%). $^1$H NMR, CDCl$_3$, δ 9.02 (d, J=8.6 Hz, 1H), 7.64–7.25 (m, 14H), 5.50 (d, J=8.6 Hz, 1H), 4.54 (septet, J=7.0 Hz, 1H), 3.70 (dd, J=3.9, 9.8 Hz, 1H), 3.34 (dd, J=3.9, 13.8 Hz, 1H), 2.82 (dd, J=9.8, 13.8 Hz, 1H), 1.51–1.40 (m, 5H), 1.27 (d, J=7.0 Hz, 1H).

The absolute stereochemistry at C-3 of the benzodizepine ring was determined to be "R" by single crystal X-Ray analysis The slower running diastereomer was recovered as a white solid (5.0 g, 16%). $^1$H NMR, CDCl$_3$, δ 9.05 (d, J=8.5 Hz, 1H), 7.63–7.20 (m, 14H), 5.48 (d, J=8.5 Hz, 1H), 4.56 (septet, J=7.0 Hz, 1H), 3.74 (dd, J=4.3, 10.0 Hz, 1H), 3.37 (dd, J=4.3, 13.8 Hz, 1H), 2.68 (dd, J=10.0, 13.8 Hz, 1H), 1.55–1.39 (m, 5H), 1.29 (d, J=7.0 Hz, 1H).

Step E: Preparation of 3R-(+) and 3S-(−) 3-Amino-2,3-dihydro-1-(2-propyl)-2-oxo-5-phenyl-1H-benzo[e][1,4]diazepine To a stirring solution of (2R)-2-amino-3-phenyl-N-[3R-2,3-dihydro-1-(2-propyl)-2-oxo-5-phenyl-1H-benzo[e][1,4] diazepin-3-yl]propionamide (the faster running diastereomer from step D)(22 g, 49.9 mmol) in methylene chloride (100 mL) was added phenylisothiocyanate (7.17 mL, 59.9 mmol) and the resulting solution was stirred for 16 h. The reaction mixture was concentrated under reduced pressure to yield a yellowish oil which was cooled in an ice/water bath. Trifluoroacetic acid (40 mL, 500 mmol) was added dropwise to the oil and the resulting solution was allowed to warm to ambient temperature over 2.5 h. The reaction mixture was concentrated under reduced pressure to yield a yellowish oil which was chromatographed over silica (1 kg) with 90:10:1:1 methylene chloride: methanol: acetic acid: water. The resulting white foam was crystallized from ethyl acetate/hexane to give The 3R-(+) enantiomer as a white solid (9.5 g, 65%). MP=155°–157° C.;

$^1$H NMR, CDCl$_3$, δ 7.63–7.20 (m, 9H), 4.58 (septet, J=7.0 Hz, 1H), 4.41 (s, 1H), 2.43 (s, 2H), 1.50 (d, J=7.0 Hz, 3H), 1.23 (d, J=7.0 Hz, 3H). [α]D=+150° (c=0.63; MeOH)

The 3S-(−) enantiomer was prepared in the same fashion by starting with the slower running diastereomer from step D.

MP=155°–157° C.;

$^1$H NMR, CDCl$_3$, δ 7.63–7.20 (m, 9H), 4.58 (septet, J=7.0 Hz, 1H), 4.41 (s, 1H), 2.43 (s, 2H), 1.50 (d, J=7.0 Hz, 3H), 1.23 (d, J=7.0 Hz, 3H). [α]D=−159° (c=0.83, MeOH)

Step F: Preparation of (+)-3-(3,5-Dichloro)-N-[2,3-dihydro-1-(2-propyl)-2-oxo-5-phenyl-1H-benzo[e][1,4]diazepin-3-yl] benzamide To a stirring solution of (+)3R-3-amino-2,3-dihydro-1-(2-propyl)-2-oxo-5-phenyl-1H-1,4-benzodiazepine (5.2 g, 17.7 mmol) in dimethylformamide (20 mL) was added EDC (4.08 g, 21.3 mmol), HOBT (2.87 g, 21.3 mmol) and 3,5-dichlorobenzoic acid (4.06 g, 21.3 mmol). This was stirred at ambient temperature for 2 h. The reaction was diluted with saturated aqueous sodium hydrogen carbonate (700 mL) and extracted with ethyl acetate (3×500 mL). The organic layers were combined, dried with brine, anhydrous magnesium sulfate, filtered, and evaporated under reduced pressure to give a colorless oil which was chromatographed over silica with 10 to 30% ethyl acetate/hexane. The resulting foam was crystallized from ethyl acetate/hexane to give a white solid (6.7 g, 81%). mp=141°–142° C., [α]D=+80.6° (c=0.74; MeOH), $^1$H NMR, CDCl$_3$, δ 8.03 (d, J=7.8 Hz, 1H), 7.80–7.20 (m, 12H), 5.61 (d, J=7.8 Hz, 1H), 4.58 (septet, J=7.0 Hz, 1H), 1.52 (d, J=7.0 Hz, 3H), 1.32 (d, J=7.0 Hz, 3H).

Anal. Calcd. for C$_{25}$H$_{21}$N$_3$O$_2$Cl$_2$:
C, 63.89; H, 4.59; N, 8.94. Found: C, 63.87; H, 4.70; N, 8.88%.

The following examples were prepared by a procedure substantially as described for Example 1 step F from either the 3R-(+) or the 3S-(−) amine enantiomer obtained in step E.

EXAMPLE 2

(+)-3-Cyclohexyl-N-[3R-2,3-dihydro-1-(2-propyl)-2-oxo-5-phenyl-1H-benzo[e][1,4]diazepin-3-yl]propanamide

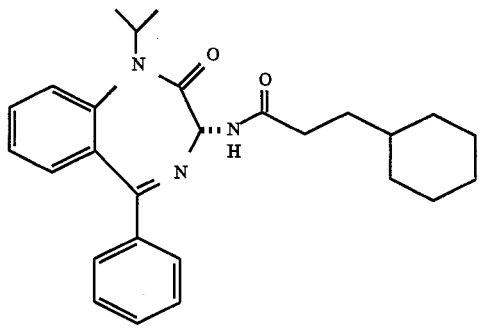

mp=154°–155° C.

[α]D=+58.7° (c=0.77; MeOH)

$^1$H NMR, CDCl$_3$, δ 7.60–7.13 (m, 10H), 5.48 (d, J=8.3 Hz, 1H), 4.53 (septet, J=6.9 Hz, 1H), 2.40–2.34 (m, 2H), 1.80–1.43 (m, 10H), 1.39–1.10 (m, 7H), 1.01–0.92 (m, 2H).

Anal. Calcd. for C$_{27}$H$_{33}$N$_3$O$_2$:

C, 75.14; H, 7.71; N, 9.74. Found: C, 75.28; H, 7.71; N, 9.86%.

EXAMPLE 3

(+)-2-(3,4-Dichlorophenyl)-N-[3R-2,3-dihydro-1-(2-propyl)-2-oxo-5-phenyl-1H-benzo[e][1,4]diazepin-3-yl] acetamide

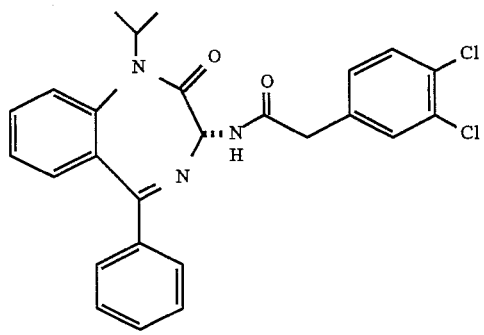

mp=171°–172° C.

[α]D=+37.0° (c=0.61; MeOH)

¹H NMR, CDCl₃, δ 7.59–7.19 (m, 10H), 5.44 (d, J=8.3 Hz, 1H), 4.54 (septet, J=6.9 Hz, 1H), 3.54 (s, 2H), 1.49 (d, J=6.9 Hz, 3H), 1.25 (d, J=6.9 Hz, 3H).

Anal. Calcd. for $C_{26}H_{23}N_3O_2Cl_2$: C, 65.01; H, 4.83; N, 8.75. Found: C, 65.00; H, 4.89; N, 8.71%.

EXAMPLE 4

(+)-2-(3,5-Dichlorophenyl)-N-[3R-2,3-dihydro-1-(2-propyl)-2-oxo-5-phenyl-1H-benzo[e][1,4]diazepin-3-yl]acetamide

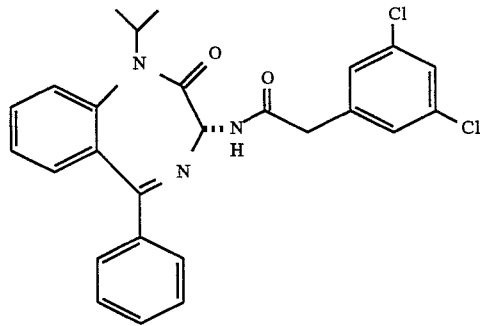

mp=90°–96° C.

[α]D=+42.7° (c=0.71; MeOH)

¹H NMR, CDCl₃, δ 7.59–7.19 (m, 10H), 5.44 (d, J=8.3 Hz, 1H), 4.54 (septet, J=6.9 Hz, 1H), 3.54 (s, 2H), 1.49 (d, J=6.9 Hz, 3H), 1.25 (d, J=6.9 Hz, 3H).

Anal. Calcd. for $C_{26}H_{23}N_3O_2Cl_2 \cdot 0.20\ H_2O$:

C, 64.52; H, 4.87; N, 8.68. Found: C, 64.55; H, 5.00; N, 8.54%.

EXAMPLE 5

(+)-3-(2,4-Dichlorophenyl)-N-[3R-2,3-dihydro-1-(2-propyl)-2-oxo-5-phenyl-1H-benzo[e][1,4]diazepin-3-yl]propanamide

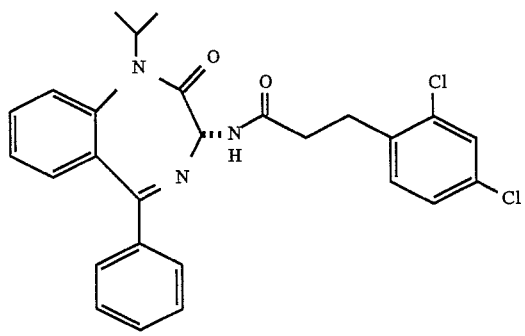

m.p. 138°–139° C., [α]D=+70.9° (c=0.79; MeOH).

Anal. Calcd. for $C^{27}H_{25}N_3O_2Cl_2$:

C, 65.59; H, 5.1; N, 8.5. Found: C, 65.21; H, 5.1; N, 8.6%.

EXAMPLE 6

(−)-3-(2,4-Dichlorophenyl)-N-[3S-2,3-dihydro-1-(2-propyl)-2-oxo-5-phenyl-1H-benzo[e][1,4]diazepin-3-yl]propanamide

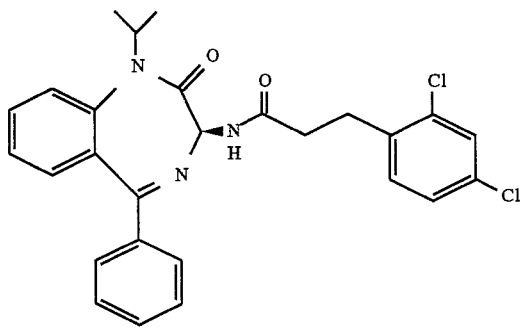

m.p. 142°–143° C., [α]D=−66.3° (c=0.64; MeOH).

Anal. Calcd. for $C_{27}H_{25}N_3O_2Cl_2$:

C, 65.59; H, 5.1; N, 8.5. Found: C, 65.51; H, 5.04; N, 8.65%.

EXAMPLE 7

(−)-3-(3,4-Dichloro)-N-[3S-2,3-dihydro-1-(2-propyl)-2-oxo-5-phenyl-1H-benzo[e][1,4]diazepin-3-yl]benzamide

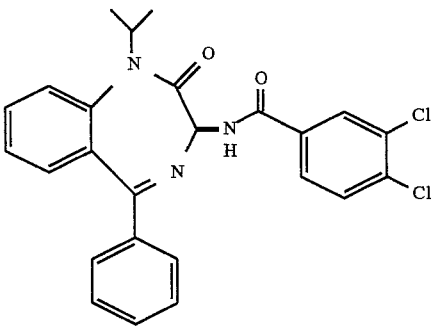

m.p. 143°–144° C., [α]D=−72.2° (c=0.45; MeOH).

Anal. Calcd. for $C_{25}H_{21}N_3O_2Cl_2 \cdot 0.55$ mol cyclohexane: C, 66.3; H, 5.43; N, 8.2. Found: C, 66.31; H, 5.49; N, 8.19%.

EXAMPLE 8

(+)-2-(Adamantan-1-yl)-N-[3R-2,3-dihydro-1-(2-propyl)-2-oxo-5-phenyl-1H-benzo[e][1,4]diazepin-3-yl]acetamide

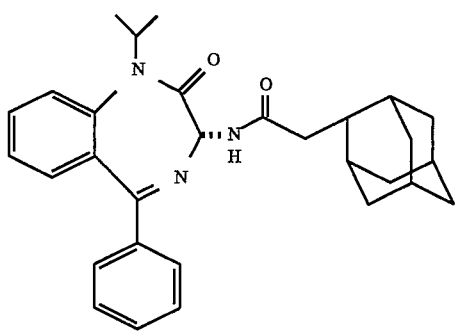

m.p. 176°–177° C., [α]D=+63.5° (c=0.51; MeOH).
Anal. Calcd. for $C_{30}H_{35}N_3O_2$:
C, 76.73; H, 7.51; N, 8.95. Found: C, 76.39; H, 7.46; N, 8.86%.

EXAMPLE 9

(+)-4-Cyclohexyl-N-[3R-2,3-dihydro-1-(2-propyl)-2-oxo-5-phenyl-1H-benzo[e][1,4]diazepin-3-yl]butanamide

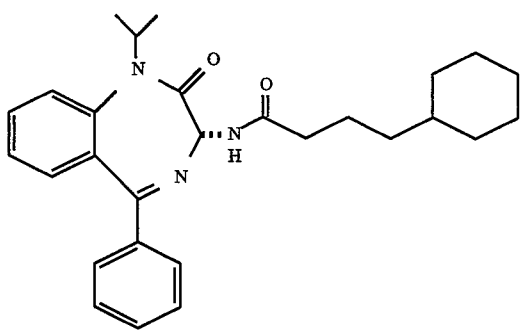

m.p. foam °C., [α]D=+59.1°(c=0.43; MeOH)..
Anal. Calcd. for $C_{28}H_{35}N_3O_2 \cdot 0.20$ mol H2O:
C, 74.87; H, 7.94; N, 9.35. Found: C, 74.92; H, 7.88; N, 9.35%.

EXAMPLE 10

(+)-Adamantan-1-yl-N-[3R-2,3-dihydro-1-(2-propyl)-2-oxo-5-phenyl-1H-benzo[e][1,4]diazepin-3-yl]carboxamide

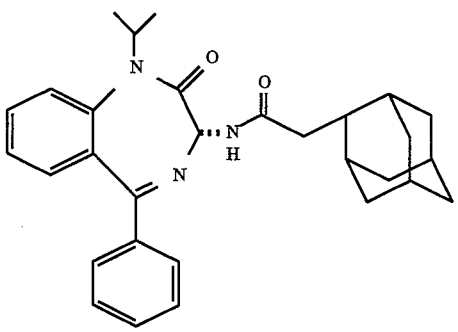

m.p. 206°–207° C., [α]D=+38.5° (c=0.52; MeOH).
Anal. Calcd. for $C_{29}H_{33}N_3O_2 \cdot 0.30$ mol H2O:
C, 75.56; H, 7.35; N, 9.11. Found: C, 75.62; H, 7.33; N, 8.91%.

EXAMPLE 11

(+)-2-[3,5-Bis(trifluoromethyl)phenyl]-N-[3R-2,3-dihydro-1-(2-propyl)-2-oxo-5-phenyl-1H-benzo[e][1,4]diazepin-3-yl]acetamide

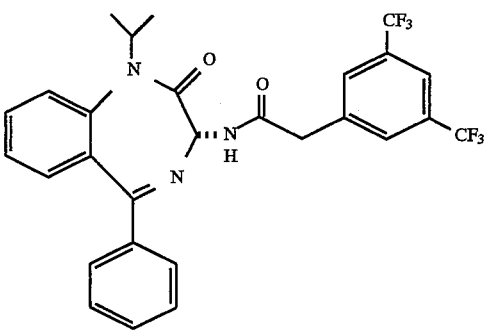

m.p. 152°–153° C., [α]D=+37.5° (c=0.65; MeOH).

Anal. Calcd. for $C_{28}H_{23}N_3O_2F_6$:

C, 61.43; H, 4.23; N, 7.67. Found: C, 61.47; H, 4.22; N, 7.7%.

EXAMPLE 12

(+)-2-(2,4-Dichlorophenyl)-N-[3R-2,3-dihydro-1-(2-propyl)-2-oxo-5-phenyl-1H-benzo[e][1,4]diazepin-3-yl]acetamide

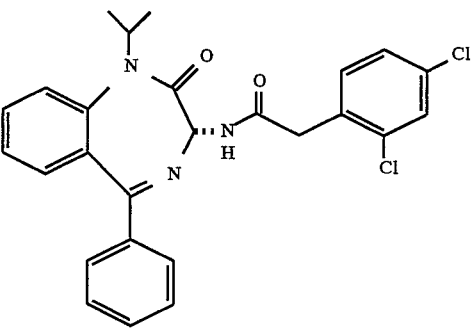

m.p. 78°–84° C., [α]D=+26.3° (c=0.67; MeOH).

Anal. Calcd. for $C_{26}H_{23}N_3O_2Cl_2 \cdot 0.20$ mol cyclohexane:

C, 65.7; H, 5.15; N, 8.45. Found: C, 65.53; H, 5.25; N, 8.35%.

EXAMPLE 13

(+)-3-Chloro-N-[3R-2,3-dihydro-1-(2-propyl)-2-oxo-5-phenyl-1H-benzo[1,4]diazepin-3-yl]benzamide

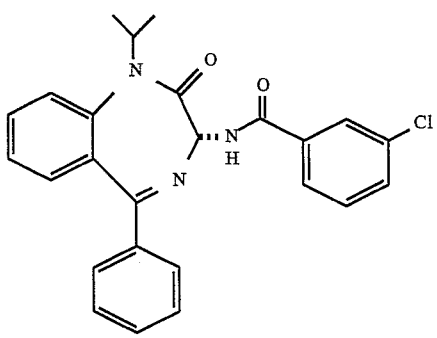

m.p. 79°–86° C., [α]D=+50.5° (c=0.55; MeOH).

Anal. Calcd. for $C_{25}H_{22}N_3O_2Cl.0.35$ mole cyclohexane:

C, 70.55; H, 5.72; N, 9.11. Found: C, 70.63; H, 5.79; N, 9.18%.

EXAMPLE 14

(+)-4-Chloro-N-[3R-2,3-dihydro-1-(2-propyl)-2-oxo-5-phenyl-1H-benzo[e][1,4]diazepin-3-yl]benzamide

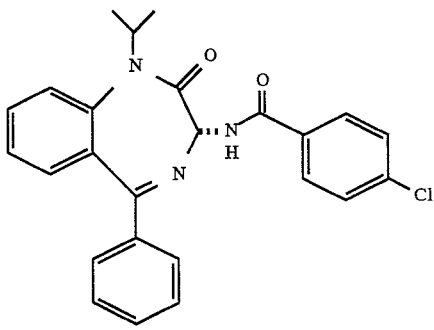

m.p. 168°–169° C., [α]D=+79.7° (c=0.96; MeOH).

Anal. Calcd. for $C_{25}H_{22}N_3O_2Cl$:

C, 69.52; H, 5.13; N, 9.73. Found: C, 69.75; H, 5.19; N, 9.9%.

EXAMPLE 15

(+)-2-(3-Chlorophenyl)-N-[3R-2,3-dihydro-1-(2-propyl)-2-oxo-5-phenyl-1H-benzo[e][1,4]diazepin-3-yl]acetamide

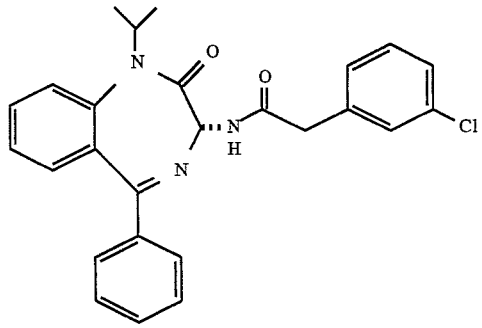

m.p. 137°–139° C., [α]D=+44.2° (c=0.60; MeOH).

Anal. Calcd. for $C_{26}H_{24}N_3O_2Cl$:

C, 70.03; H, 5.42; N, 9.42. Found: C, 70.23; H, 5.43; N, 9.45%.

EXAMPLE 16

(+)-3-Bromo-4-chloro-N-[3R -2,3-dihydro-1-(2-propyl)-2-oxo-5-phenyl-1H-benzo[e][1,4]diazepin-3-yl]benzamide

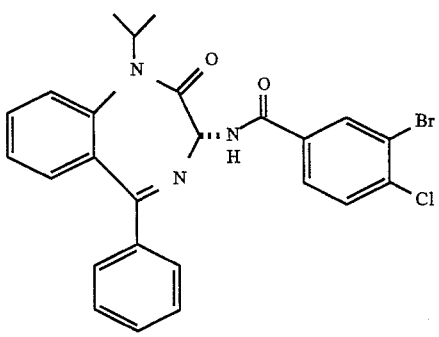

m.p. 173°–175° C., [α]D=+58.6° (c=0.36; MeOH).

Anal. Calcd. for $C_{25}H_{20}N_3O_2BrCl.0.40$ mol $H_2O$:

C, 58.08; H, 4.06; N, 8.13. Found: C, 58.1; H, 4.14; N, 8.11%.

EXAMPLE 17

(+)-3-Bromo-N-[3R-2,3-dihydro-1-(2-propyl)-2-oxo-5-phenyl-1H-benzo[e][1,4]diazepin-3-yl]benzamide

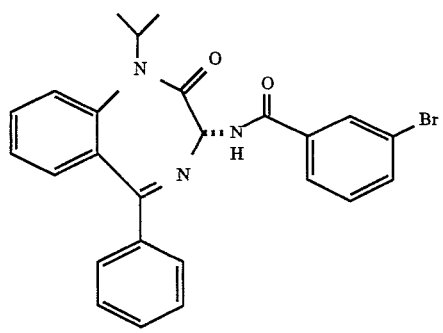

m.p. 78°–85° C., [α]D=+50.4° (c=0.76; MeOH).

Anal. Calcd. for $C_{25}H_{22}N_3O_2Br.0.85$ mol $H_2O$ 0.30 mol cyclohexane:

C, 62.27; H, 5.32; N, 8.13. Found: C, 62.27; H, 5.16; N, 8.03%.

EXAMPLE 18

(−)-3,5-Dichloro-N-[3S-2,3-dihydro-1-(2-propyl)-2-oxo-5-phenyl-1H-benzo[e][1,4]diazepin-3-yl]benzamide

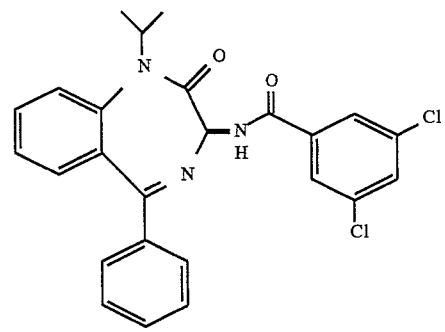

m.p. 140°–141° C., [α]D=−83.7° (c=0.52; MeOH).

Anal. Calcd. for $C_{25}H_{21}N_3O_2Cl_2$:

C, 64.39; H, 4.54; N, 9.01. Found: C, 64.36; H, 4.76; N, 8.62%.

EXAMPLE 19

(+)-N-[3R-2,3-dihydro-1-(2-propyl)-2-oxo-5-phenyl-1H-benzo[e][1,4]diazepin-3-yl]benzamide

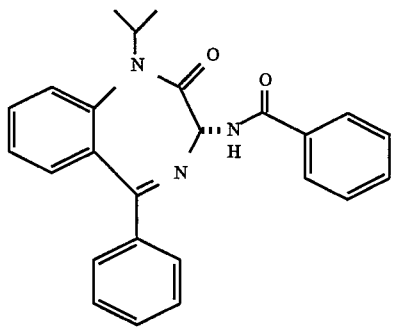

m.p. 216°–219° C., [α]D+53.9° (c=0.36; CHCl3).

Anal. Calcd. for $C_{25}H_{23}N_3O_2$:

C, 75.55; H, 5.83; N, 10.57. Found: C, 75.9; H, 5.87; N, 10.69%.

EXAMPLE 20

(+)-2-(3-Trifluoromethylphenyl)-N-[3R-2,3-dihydro-1-(2-propyl)-2-oxo-5-phenyl-1H-benzo[e][1,4]diazepin-3-yl]acetamide

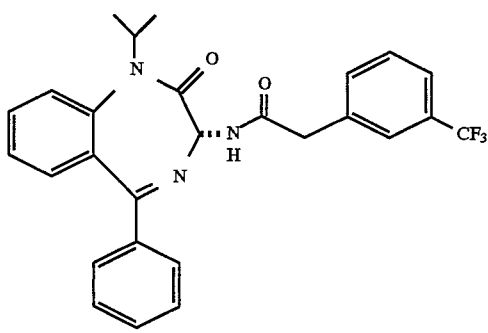

[α]D+35.9° (c=0.41; MeOH).

Anal. Calcd. for $C_{27}H_{24}N_3O_2F_3$:

C, 67.63; H, 5.05; N, 8.76. Found: C, 67.96; H, 5.27; N, 8.37%.

EXAMPLE 21

(+)-3,5-Bis(trifluoromethyl)-N-[3R-2,3-dihydro-1-(2-propyl)-2-oxo-5-phenyl-1H-benzo[e][1,4]diazepin-3-yl]benzamide

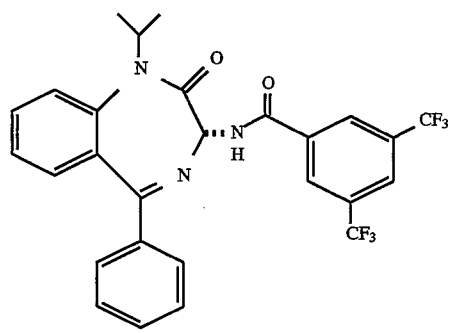

m.p. 198°–199° C., [α]D+39.2° (c=0.53; MeOH).

Anal. Calcd. for $C_{27}H_{21}N_3O_2F_6$.0.40 mol EtOAc:

C, 60.4; H, 4.29; N, 7.39. Found: C, 60.4; H, 4.28; N, 7.42%.

EXAMPLE 22

(+)-2-(2-Trifluoromethylphenyl)-N-[3R-2,3-dihydro-1-(2-propyl)-2-oxo-5-phenyl-1H-benzo[e][1,4]diazepin-3-yl]acetamide

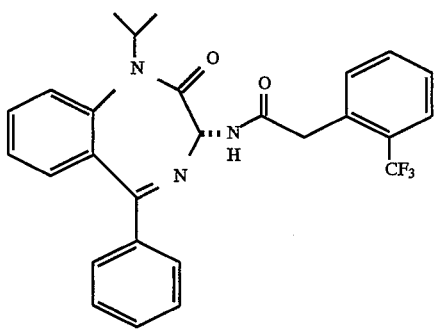

m.p. 160°–162° C., [α]D+32.3° (c=0.39; MeOH).

Anal. Calcd. for $C_{27}H_{24}N_3O_2F_3$:

C, 67.63; H, 5.05; N, 8.76. Found: C, 67.58; H, 5.1; N, 8.85%.

EXAMPLE 23

(+)-2-(4-Trifluoromethylphenyl)-N-[3R-2,3-dihydro-1-(2-propyl)-2-oxo-5-phenyl-1H-benzo[e][1,4]diazepin-3-yl]acetamide

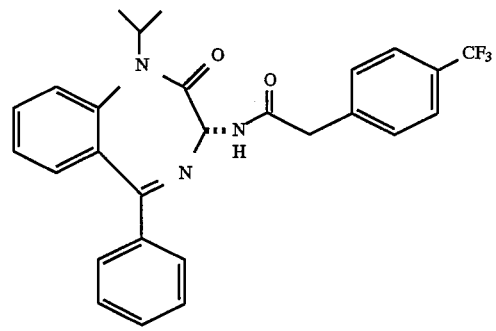

m.p. 227°–228° C., [α]D+38.0° (c=0.30; MeOH).

Anal. Calcd. for $C_{27}H_{24}N_3O_2F_3$:

C, 67.63; H, 5.05; N, 8.76. Found: C, 67.93; H, 5.06; N, 8.98%.

EXAMPLE 24

(+)-2-Phenyl-N-[3R-2,3-dihydro-1-(2-propyl)-2-oxo-5-phenyl-1H-benzo[e][1,4]diazepin-3-yl]acetamide

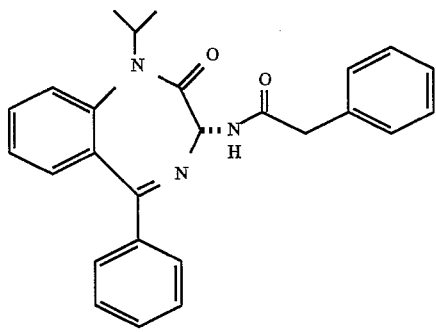

m.p. 154°–156° C., [a]d+40.3° (c=0.38; MeOH).

Anal. Calcd. for C<sub>26</sub>H<sub>25</sub>N<sub>3</sub>O<sub>2</sub>.0.45 mol H2O:

C, 74.42; H, 6.22; N, 10.01. Found: C, 74.45; H, 6; N, 9.96%.

EXAMPLE 25

(−)-2-(3,5-Dichlorophenyl)-N-[3S-2,3-dihydro-1-(2-propyl)-2-oxo-5-phenyl-1H-benzo[e][1,4]diazepin-3 -yl]acetamide

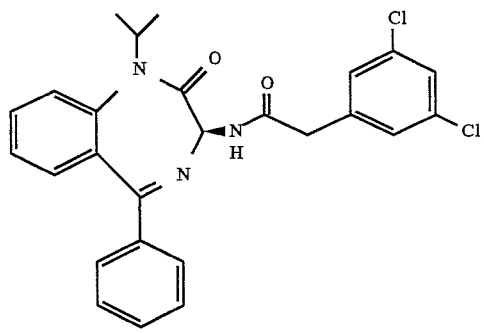

m.p. foam °C., [α]D=−39.1° (c=0.46; MeOH).

Anal. Calcd. for C<sub>26</sub>H<sub>23</sub>N<sub>3</sub>O<sub>2</sub>Cl<sub>2</sub>:

C, 65.01; H, 4.83; N, 8.75. Found: C, 64.69; H, 4.85; N, 8.55%.

EXAMPLE 26

(−)-2-Hydroxy-2-(4-trifluoromethylphenyl)-N-[1-(2-propyl)-2-oxo-5-phenyl-2,3-dihydro-1H-benzo[e][1,4]diazepin-3-yl]acetamide

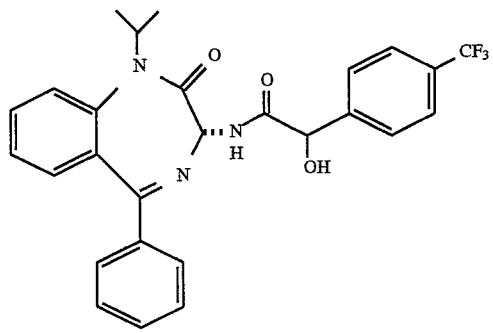

m.p. 195°–6° C., [α]D=−33° (c=0.49; MeOH).

Anal. Calcd. for C<sub>27</sub>H<sub>24</sub>N<sub>3</sub>O<sub>3</sub>F<sub>3</sub>:

C, 65.45; H, 4.88; N, 8.48. Found: C, 65.19; H, 4.83; N, 8.35%.

EXAMPLE 27

(+)-2-Hydroxy-2-(4-trifluoromethylphenyl)-N-[1-(2-propyl)-2-oxo-5-phenyl-2,3-dihydro-1H-benzo[e][1,4]diazepin-3-yl]acetamide

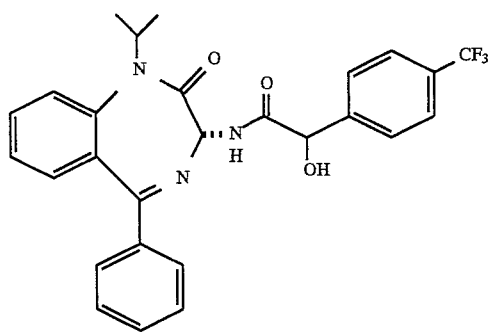

m.p. 227–8° C., [α]D=+53° (c=0.89; MeOH).

Anal. Calcd. for C<sub>27</sub>H<sub>24</sub>N<sub>3</sub>O<sub>3</sub>F<sub>3</sub>:

C, 65.45; H, 4.88; N, 8.48. Found: C, 65.26; H, 4.82; N, 8.55%.

EXAMPLE 28

(+)-2-[2,4-Bis(trifluoromethyl)phenyl]-N-[3R-2,3-dihydro-1-(2-propyl)-2-oxo-5-phenyl-1H-benzo[e][1,4]diazepin-3-yl]acetamide

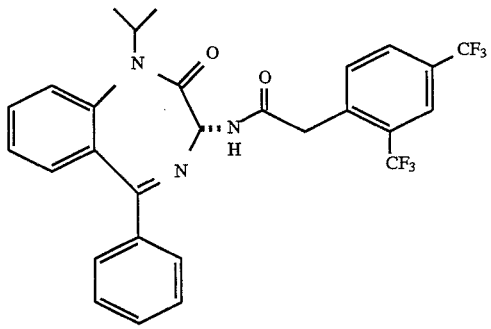

Step A. 2,4-Bis(trifluoromethyl)benzonitrile

To a stirring biphasic mixture of 100 mL ethanol and 250 mL of phosphate buffer (1 g of NaH<sub>2</sub>PO<sub>4</sub>.H<sub>2</sub>O per 5 mL H<sub>2</sub>O adjusted to pH=7.0 with 50% NaOH) and NaCN (81.3 mmol, 4.0 g) heated to 60° C. was added 2,4-bis (trifluoromethyl) benzyl bromide (32.5 mmol, 10 g) in 50 mL EtOH dropwise over 30 min. The reaction was heated at 60° C. for 24 h. The reaction was then evaporated under reduced pressure. The remaining aqueous was extracted with 2×150 mL EtOAc. The organic layers were combined, dried with brine and $Na_2SO_4$. The organic phase was evaporated under reduced pressure and the residue chromatographed over silica eluting with 10% EtOAc:Hexanes. The pure fractions were collected and evaporated to give 7.0 g of a pale yellow oil, 85.1% NMR $^1H$ (CDCl$_3$) δ 8.0–7.85 (m, 3H), 4.03 (s, 2H)

Step B. 2,4-Bis(trifluoromethyl)phenyl acetic acid 2,4-Bis(trifluoromethyl)benzonitrile (41.5 mmol, 10.51 g) was taken up in 100 mL acetic acid, 50 mL conc. $H_2SO_4$, and 20 mL water. This was heated to 120° C. for 3 h. The reaction was then diluted with 1 L ice water, and extracted with 2×300 mL ethyl acetate. The combined organics were washed with 2×200 mL water, dried with brine and $Na_2SO_4$, and evaporated under reduced pressure. The residue was taken up in a minimum of diethyl ether and crystallized by adding sufficient hexane to precipatate the product. The solid was collected to give 7.74 g of 2,4-bis(trifluoromethyl) phenyl acetic acid as white crystals, 68.5%. NMR $^1H$ (CDCl$_3$) δ 7.93 (s, 1H), 7.80 (d, J=7.9 Hz,1H), 7.55 (d, J=7.9 Hz, 1H), 3.94 (s, 2H).

Step C: (+)-2-[2,4-Bis(trifluoromethyl)phenyl]-N-[3R-2,3-dihydro-1-(2-propyl)-2-oxo-5-phenyl-1H-benzo[e][1,4]diazepin-3-yl]acetamide The 2,4-Bis-(trifluoromethyl) phenyl acetic acid obtained in step B was coupled with 3R-3-Amino-2,3-dihydro-1-(2-propyl)-2-oxo-5-phenyl-1H-benzo[e][1,4]diazepine from step E example 1 by a procedure substantially as described for step F example 1 to give (+)-2-[2,4-Bis(trifluoromethyl) phenyl]-N-[3R-2,3-dihydro-1-(2-propyl)-2-oxo-5-phenyl-1H-benzo[e][1,4]diazepin-3-yl]-acetamide m.p. 134°–136° C., [α]D+22° (c=0.39; MeOH).

Anal. Calcd. for $C_{28}H_{23}N_3O_2F_3$:

C, 61.43; H, 4.23; N, 7.67. Found: C, 61.61; H, 4.24; N, 7.75%.

The following examples were prepared by procedures substantially as described in example 1 except substituting the appropriate fluoro substituted aminobenzophenone in step A.

EXAMPLE 29

(+)-3-Cyclohexyl-N-[2,3-dihydrol-(2-propyl)-2-oxo-5-(4-fluoroprophenyl)-1H-benzo[e][1,4]diazepin-3-yl] propanamide

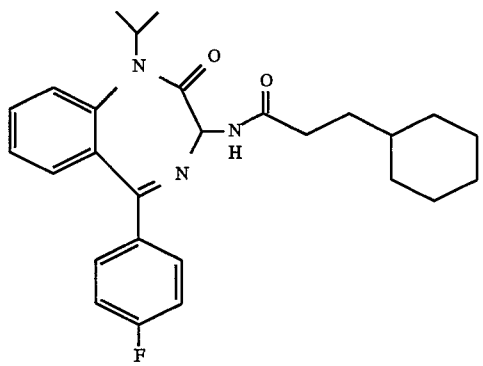

mp=179°–181° C.
[α]D=+45.1° (c=0.55; MeOH)

Anal. Calcd. for $C_{27}H_{32}FN_3O_2$:

C, 72.14; H, 7.17; N, 9.35. Found: C, 71.98; H, 7.10; N, 9.43%.

EXAMPLE 30

(+)-3-5-Dichloro-N-[2,3-dihydro-1-(2-propyl)-2-oxo-5-(4-fluorophenyl)-1H-benzo[e][1,4]diazepin-3-yl]benzamide

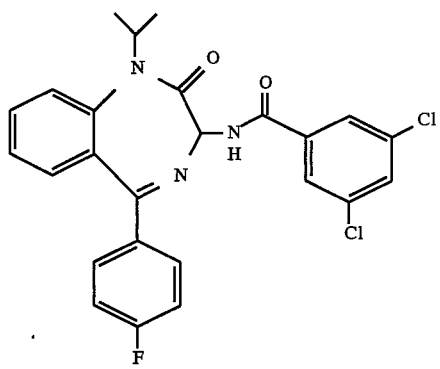

m.p. 174°–176° C., [α]D+53.9° (c=0.36; CHCl3).

Anal. Calcd. for $C_{25}H_{20}Cl_2FN_3O_2$:

C, 61.54; H, 4.21; N, 8.61. Found: C, 61.54; H, 4.22; N, 8.72

EXAMPLE 31

3-Cyclohexyl-N-[2,3-dihydro-1-(2-propyl)-2-oxo-5-(2-fluorophenyl)-1H-benzo[e][1,4]diazepin-3-yl]propanamide

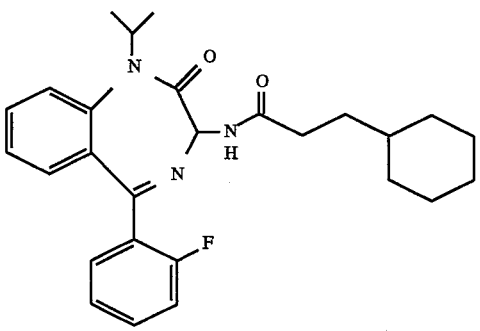

m.p. 165°–167° C.

Anal. Calcd. for $C_{27}H_{32}N_3O_2F$:

C, 72.14; H, 7.17; N, 9.35. Found: C, 71.71; H, 7.11; N, 9.33%.

EXAMPLE 32

3,4-Dichloro-N-[2,3-dihydro-1-(2-propyl)-2-oxo-5-(2-fluorophenyl)-1H-benzo[e][1,4]diazepin-3-yl]benzamide

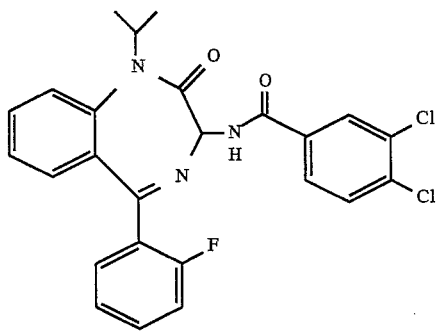

m.p. 188°–189° C.

Anal. Calcd. for $C_{25}H_{20}ON_3O_2Cl_2F$:

C, 61.99; H, 4.16; N, 8.68. Found: C, 61.7; H, 4.22; N, 8.59%.

What is claimed is:

1. A compound of the structural formula I

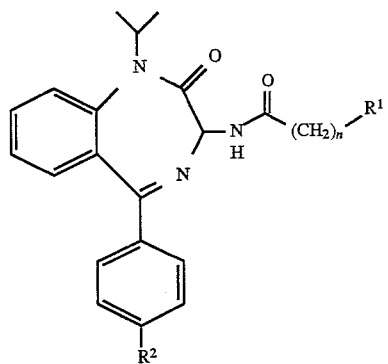

FORMULA I where

R¹ is

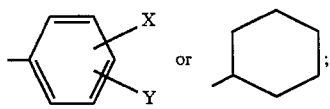

X and Y are independently hydrogen, fluoro, chloro, bromo, iodo, or trifluoromethyl;

n is 0, 1 or 2; and

R² is hydrogen, fluoro, chloro, bromo, iodo, or trifluoromethyl, methyl, or methoxy;

as the racemates, mixtures of enantiomers, individual diastereomers or individual enantiomers, and pharmaceutically acceptable crystal forms, salts, or hydrates thereof.

2. The compound of claim 1 selected from the group consisting of (+)-3,5-Dichloro-N-[3R-2,3-dihydro-1-(2-propyl)-2-oxo-5-phenyl-1H-benzo[e][1,4]diazepin-3-yl]benzamide

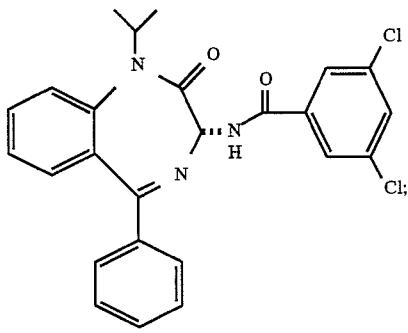

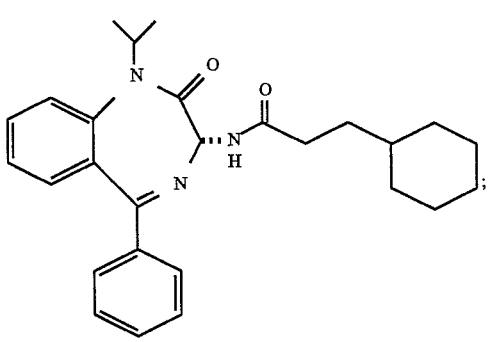

(+)-3-Cyclohexyl-N-[3R-2,3-dihydro-1-(2-propyl)-2-oxo-5-phenyl-1H-benzo[e][1,4]diazepin-3-yl]propanamide

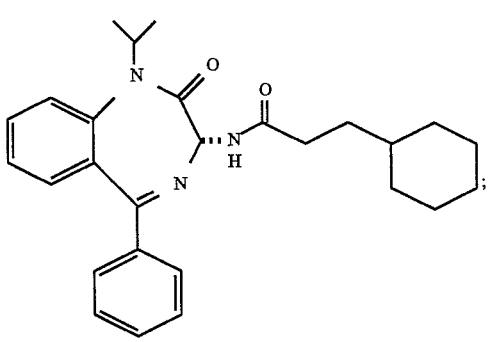

(+)-2-(3,4-Dichlorophenyl)-N-[3R-2,3-dihydro-1-(2-propyl)-2-oxo-5-phenyl-1H-benzo[e][1,4]diazepin-3-yl]acetamide

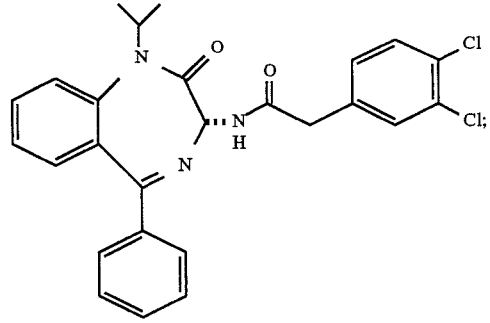

(+)-2-(3,5-Dichlorophenyl)-N-[3R-2,3-dihydro-1-(2-propyl)-2-oxo-5-phenyl-1H-benzo[e][1,4]diazepin-3-yl]acetamide

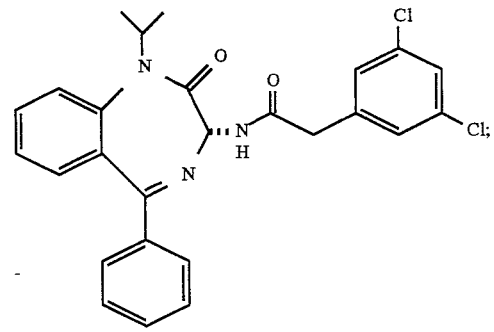

(+)-2-[2,4-Bis(trifluoromethyl)phenyl]-N-[1-(2-propyl)-2-oxo-
5-phenyl-2,3-dihydro-1H-benzo[e][1,4]diazepin-3-yl]acetamide

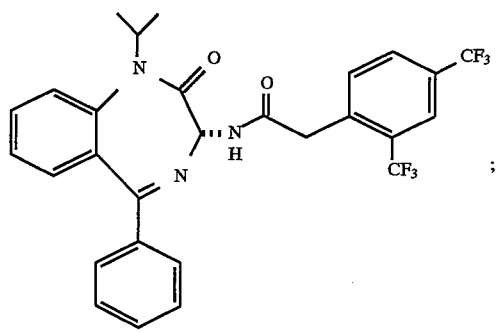

(+)-3-(2,4-Dichlorophenyl)-N-[3R-2,3-dihydro-1-(2-propyl)-2-
oxo-5-phenyl-1H-benzo[e][1,4]diazepin-3-yl]propanamide

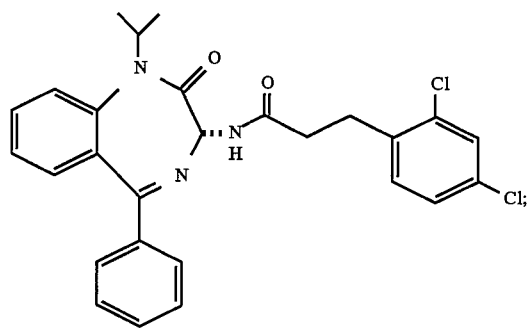

(−)-3-(2,4-Dichlorophenyl)-N-[3S-2,3-dihydro-1-(2-propyl)-
2-oxo-5-phenyl-1H-benzo[e][1,4]diazepin-3-yl]propanamide

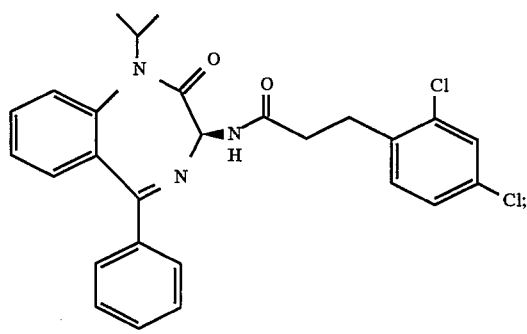

(−)-3,4-Dichloro-N-[3S-2,3-dihydro-1-(2-propyl)-2-oxo-5-
phenyl-1H-benzo[e][1,4]diazepin-3-yl]benzamide

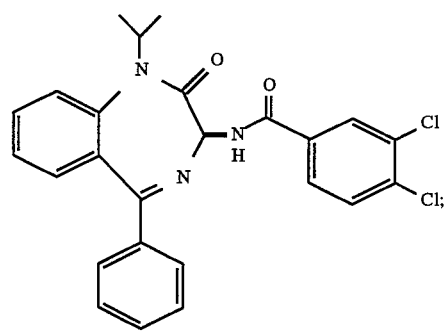

(+)-2-Adamantan-1-yl-N-[3R-2,3-dihydro-1-(2-propyl)-2-oxo-5-phenyl-
1H-benzo[e][1,4]diazepin-3-yl]acetamide

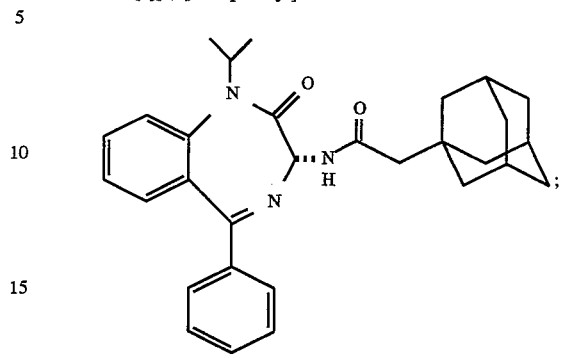

(+)-4-Cyclohexyl-N-[3R-2,3-dihydro-1-(2-propyl)-2-oxo-5-
phenyl-1H-benzo[e][1,4]diazepin-3-yl]butanamide

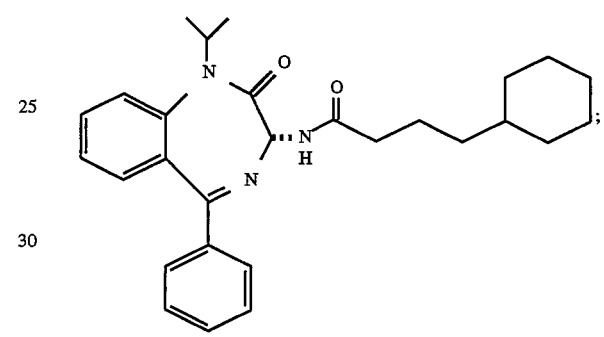

(+)-Adamantan-1-yl-N-[3R-2,3-dihydro-1-(2-propyl)-2-oxo-5-
phenyl-1H-benzo[e][1,4]diazepin-3-yl]carboxamide

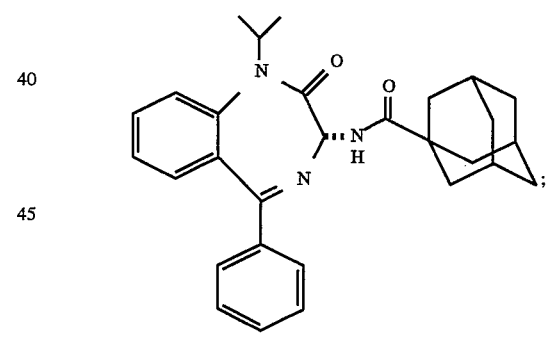

(+)-2-[3,5-Bis(trifluoromethyl)phenyl]-N-[3R-2,3-dihydro-1-(2-
propyl)-2-oxo-5-phenyl-1H-benzo[e][1,4]diazepin-3-yl]acetamide

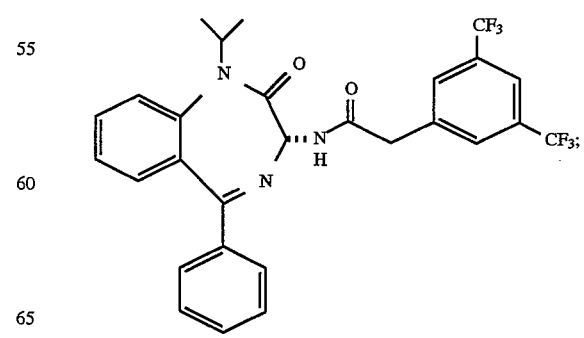

(+)-2-(2,4-Dichlorophenyl)-N-[3R-2,3-dihydro-1-(2-propyl)-2-oxo-5-phenyl-1H-benzo[e][1,4]diazepin-3-yl]acetamide

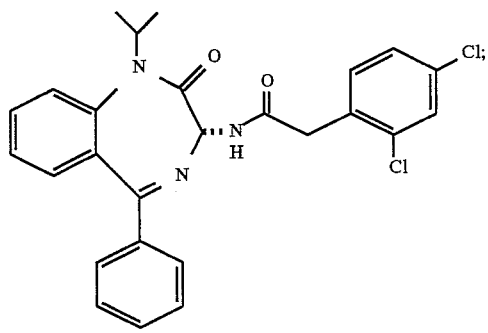

(+)-3-Chloro-N-[3R-2,3-dihydro-1-(2-propyl)-2-oxo-5-phenyl-1H-benzo[e][1,4]diazepin-3-yl]benzamide

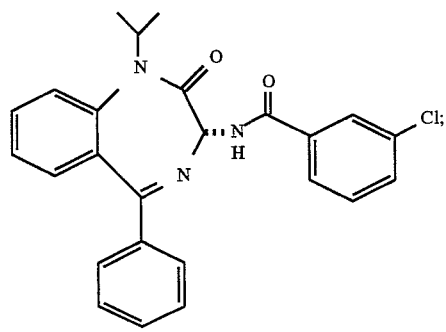

(+)-4-Chloro-N-[3R-2,3-dihydro-1-(2-propyl)-2-oxo-5-phenyl-1H-benzo[e][1,4]diazepin-3-yl]benzamide

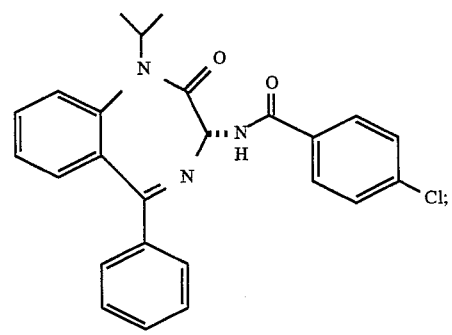

(+)-2-(3-Chlorophenyl)-N-[3R-2,3-dihydro-1-(2-propyl)-2-oxo-5-phenyl-1H-benzo[e][1,4]diazepin-3-yl]acetamide

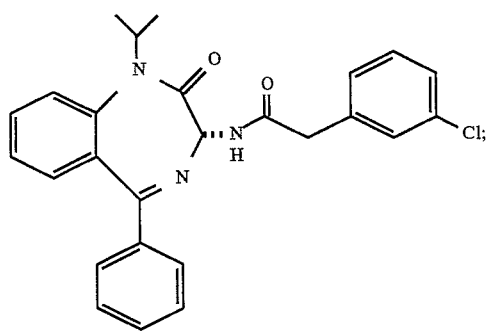

(+)-3-Bromo-4-chloro-N-[3R-2,3-dihydro-1-(2-propyl)-2-oxo-5-phenyl-1H-benzo[e][1,4]diazepin-3-yl]benzamide

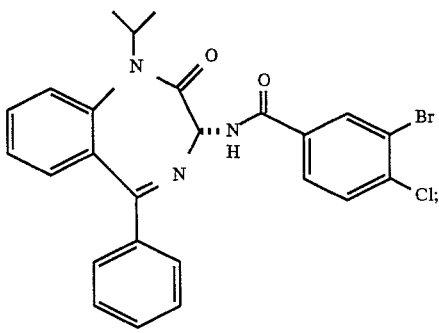

3,4-Dichloro-N-[2,3-dihydro-1-(2-propyl)-2-oxo-5-(2-fluorophenyl)-1H-benzo[e][1,4]diazepin-3-yl]benzamide

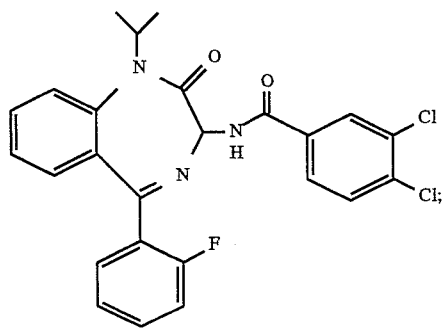

(+)-3-Bromo-N-[3R-2,3-dihydro-1-(2-propyl)-2-oxo-5-phenyl-1H-benzo[e][1,4]diazepin-3-yl]benzamide

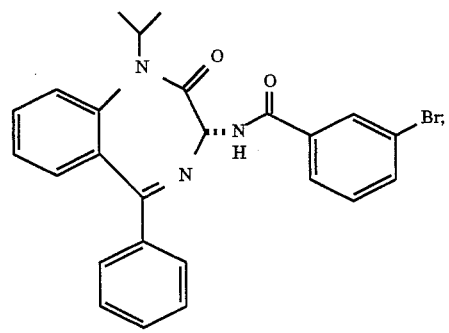

3-(Cyclohexyl)-N-[2,3-dihydro-1-(2-propyl)-2-oxo-5-(2-fluorophenyl)-1H-benzo[e][1,4]diazepin-3-yl]propanamide

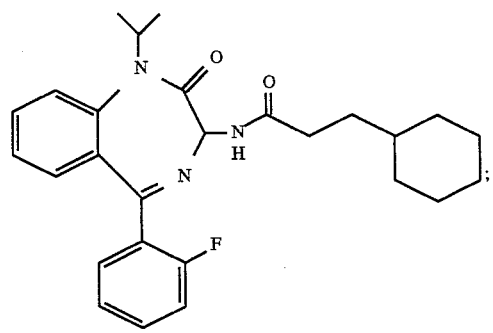

(−)-3,5-Dichloro-N-[3S-2,3-dihydro-1-(2-propyl)-2-oxo-5-phenyl-1H-benzo[e][1,4]diazepin-3-yl]benzamide

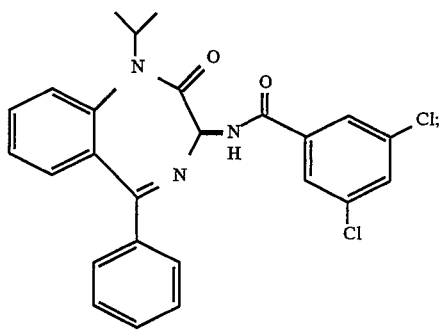

(+)-N-[3R-2,3-dihydro-1-(2-propyl)-2-oxo-5-phenyl-1H-benzo[e][1,4]diazepin-3-yl]benzamide

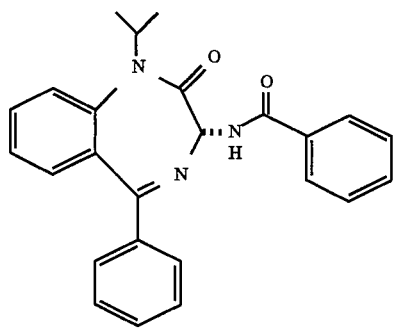

(+)-2-(3-Trifluoromethylphenyl)-N-[3R-2,3-dihydro-1-(2-propyl)-2-oxo-5-phenyl-1H-benzo[e][1,4]diazepin-3-yl]acetamide

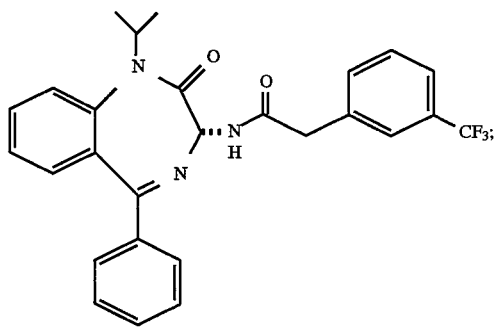

(+)-3,5-Bis(trifluoromethyl)-N-[3R-2,3-dihydro-1-(2-propyl)-2-oxo-5-phenyl-1H-benzo[e][1,4]diazepin-3-yl]benzamide

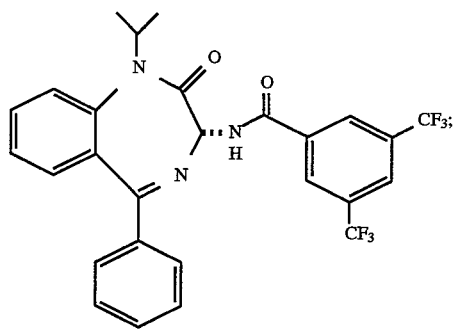

(+)-2-(2-Trifluoromethylphenyl)-N-[3R-2,3-dihydro-1-(2-propyl)-2-oxo-5-phenyl-1H-benzo[e][1,4]diazepin-3-yl]acetamide

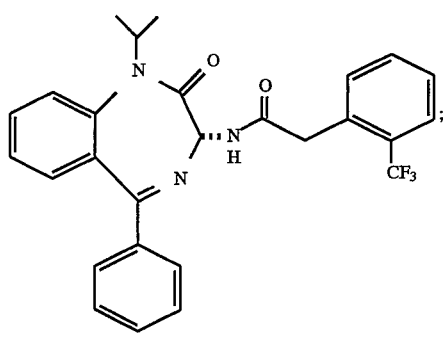

(+)-2-(4-Trifluoromethylphenyl)-N-[3R-2,3-dihydro-1-(2-propyl)-2-oxo-5-phenyl-1H-benzo[e][1,4]diazepin-3-yl]acetamide

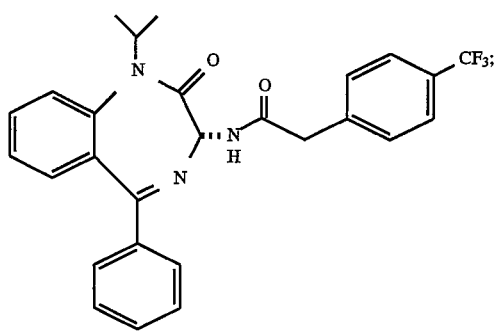

(+)-2-Phenyl-N-[3R-2,3-dihydro-1-(2-propyl)-2-oxo-5-phenyl-1H-benzo[e][1,4]diazepin-3-yl]acetamide

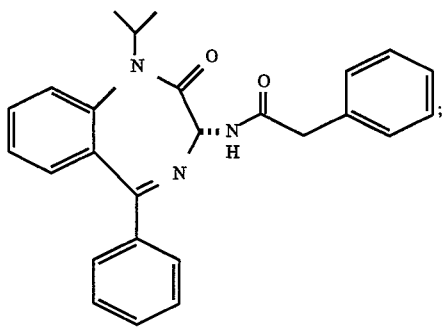

(−)-2-(3,5-Dichlorophenyl)-N-[3S-2,3-dihydro-1-(2-propyl)-2-oxo-5-phenyl-1H-benzo[e][1,4]diazepin-3-yl]acetamide

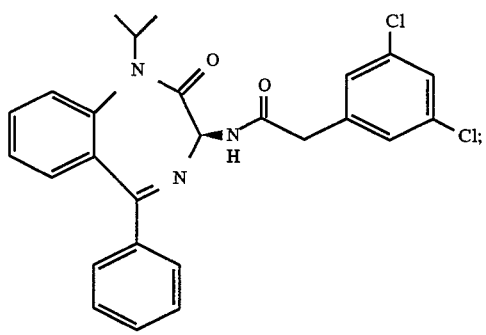

-continued (−)-3R-2-Hydroxy-2-(4-trifluoromethylphenyl)-
N-[1-(2-propyl)-2-oxo-5-phenyl-2,3-dihydro-1H-
benzo[e][1,4]diazepin-3-yl]acetamide

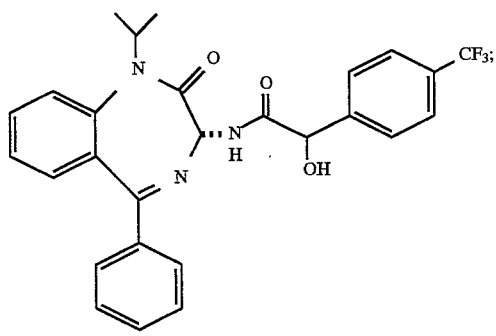

(+)-3R-2-Hydroxy-2-(4-trifluoromethylphenyl)-
N-[1-(2-propyl)-2-oxo-5-phenyl-2,3-dihydro-1H-
benzo[e][1,4]diazepin-3-yl]acetamide

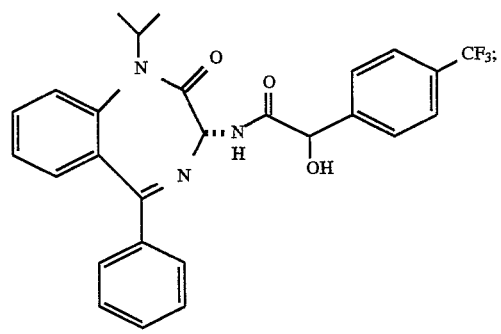

(+)-3-Cyclohexyl-N-[2,3-dihydro-1-(2-propyl)-2-oxo-5-(4-
fluorophenyl)-1H-benzo[e][1,4]diazepin-3-yl]propanamide

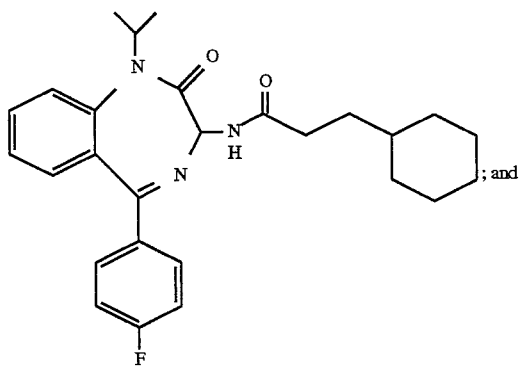

(+)-3-5-(Dichloro)-N-[2,3-dihydro-1-(2-propyl)-2-oxo-5-(4-
fluorophenyl)-1H-benzo[e][1,4]diazepin-3-yl]benzamide

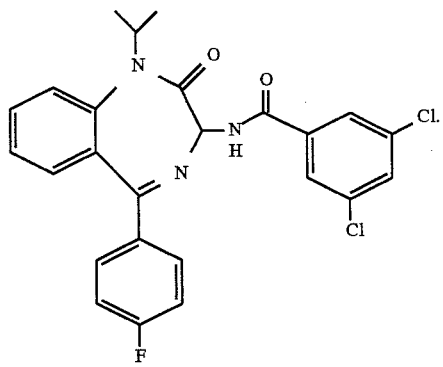

3. The compound of claim 1 which is (+)-3,5-Dichloro-
N-[3R-2,3-dihydro-1-(2-propyl)-2-oxo-5-phenyl-1H-benzo
[e][1,4]diazepin-3-yl]benzamide

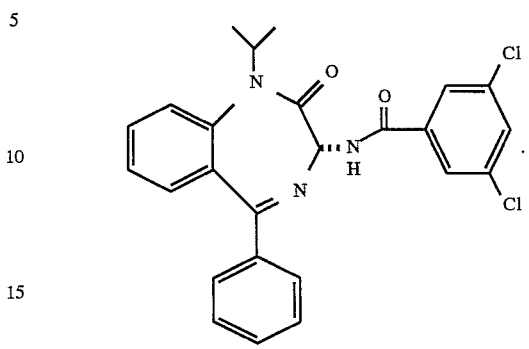

4. The compound of claim 1 which is (+)-3-Cyclohexyl-
N-[3R-2,3-dihydro-1-(2-propyl)-2-oxo-5-phenyl-1H-benzo
[e][1,4]diazepin-3-yl]propanamide

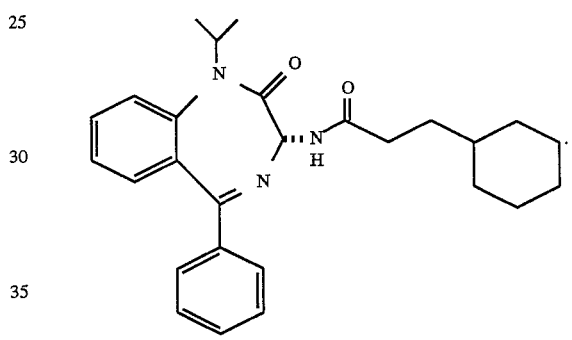

5. The compound of claim 1 which is (+)-2-(3,4-
Dichlorophenyl)-N-[3R-2,3-dihydro-1-(2-propyl)-2-oxo-5-
phenyl-1H-benzo[e][1,4]diazepin-3-yl]acetamide

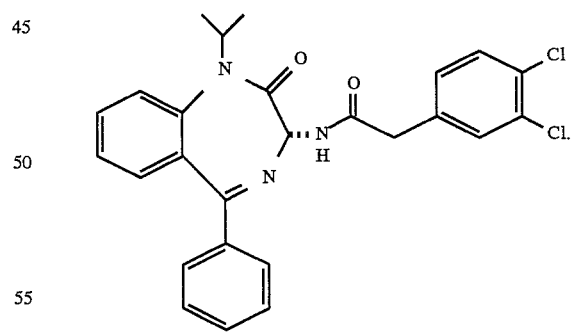

6. The compound of claim 1 which is (+)-2-(3,5-Dichlorophenyl)-N-[3R-2,3-dihydro-1-(2-propyl)-2-oxo-5-phenyl-1H-benzo[e][1,4]diazepin-3-yl]acetamide

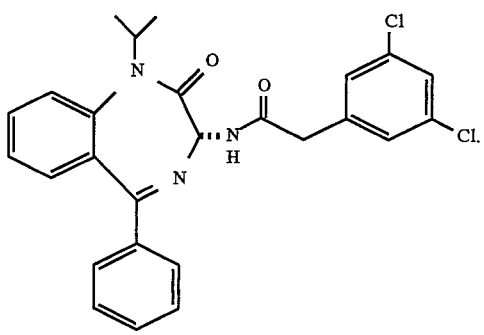

7. The compound of claim 1 which is (+)-2-[2,4-Bis-(trifluoromethyl)phenyl]-N-[3R-2,3-dihydro-1-(2-propyl)-2-oxo-5-phenyl-2,3-dihydro-1H-benzo[e][1,4]diazepin-3-yl]acetamide

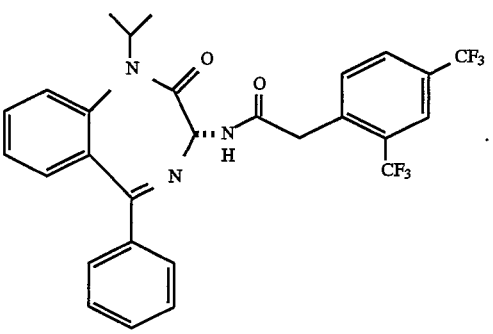

8. A pharmaceutical formulation comprising a pharmaceutically acceptable carrier and a therapeutically effective amount of the compound of claim 1 or a pharmaceutically acceptable salt, crystal form or hydrate thereof.

9. A method of preventing or treating arrhythmia which comprises the administration to a patient in need of such treatment of an antiarrhythmically effective amount of the compound of claim 1.

10. A pharmaceutical formulation comprising a pharmaceutically acceptable carrier and a therapeutically effective amount of the compound of claim 7 or a pharmaceutically acceptable salt, crystal form or hydrate thereof.

11. A method of preventing or treating arrhythmia which comprises the administration to a patient in need of such treatment of an antiarrhythmically effective amount of the compound of claim 7.

* * * * *